United States Patent [19]
Goodby et al.

[11] Patent Number: 5,861,109
[45] Date of Patent: Jan. 19, 1999

[54] LIQUID CRYSTAL MATERIALS, MIXTURES AND DEVICES

[75] Inventors: John W. Goodby; Peter Styring, both of Hull, Great Britain; Christa Loubser; Philippus L Wessels, both of Cape Town, South Africa

[73] Assignee: The Secretary of State for Defence in Her Britannic Majesty's Government of the United Kingdom of Great Britain and Northern Ireland of Defence Evaluation Research Agency, United Kingdom

[21] Appl. No.: 556,970

[22] PCT Filed: Jun. 7, 1994

[86] PCT No.: PCT/GB94/01231

§ 371 Date: Jan. 24, 1996

§ 102(e) Date: Jan. 24, 1996

[87] PCT Pub. No.: WO94/29405

PCT Pub. Date: Dec. 22, 1994

[30] Foreign Application Priority Data

Jun. 11, 1993 [GB] United Kingdom .................. 9312095

[51] Int. Cl.[6] .......................... C09K 19/12; C09K 19/20; C07D 239/02; C07C 69/76

[52] U.S. Cl. ............................... 252/299.65; 252/299.01; 252/299.61; 252/299.63; 252/299.64; 252/299.66; 252/299.67; 544/303; 544/334; 546/345; 546/346; 546/326; 570/129; 428/1; 560/65; 560/83

[58] Field of Search ....................... 252/299.01, 299.64, 252/299.65, 299.66, 299.67; 544/298, 303, 334; 546/345, 346, 326; 560/65, 83; 570/129, 127, 130, 131; 428/1

[56] References Cited

U.S. PATENT DOCUMENTS 5,167,861  12/1992  Suzuki et al. .................. 252/299.01
5,225,105   7/1993  Koseki et al. .................. 252/299.66

FOREIGN PATENT DOCUMENTS 0 332 025    9/1989  European Pat. Off. .
4013648      1/1992  Japan .
WO 92/01766  2/1992  WIPO .

OTHER PUBLICATIONS

CA 113 : 162679, 1990.

*Primary Examiner*—Shean C. Wu
*Attorney, Agent, or Firm*—Nixon & Vanderhye

[57] ABSTRACT

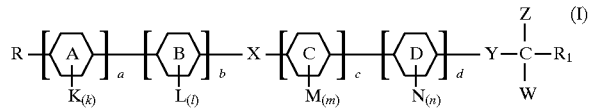

Liquid crystal compounds of formula I may be used by themselves or they may be mixed with other liquid crystal compounds to give useful liquid crystal mixtures which may then be used in liquid crystal devices. The materials exhibit smectic mesophases and may therefore be used in ferroelectric, ferrielectric, antiferroelectric, themochromic and electroclinic devices. They may also be used as long pitch materials.

17 Claims, 11 Drawing Sheets

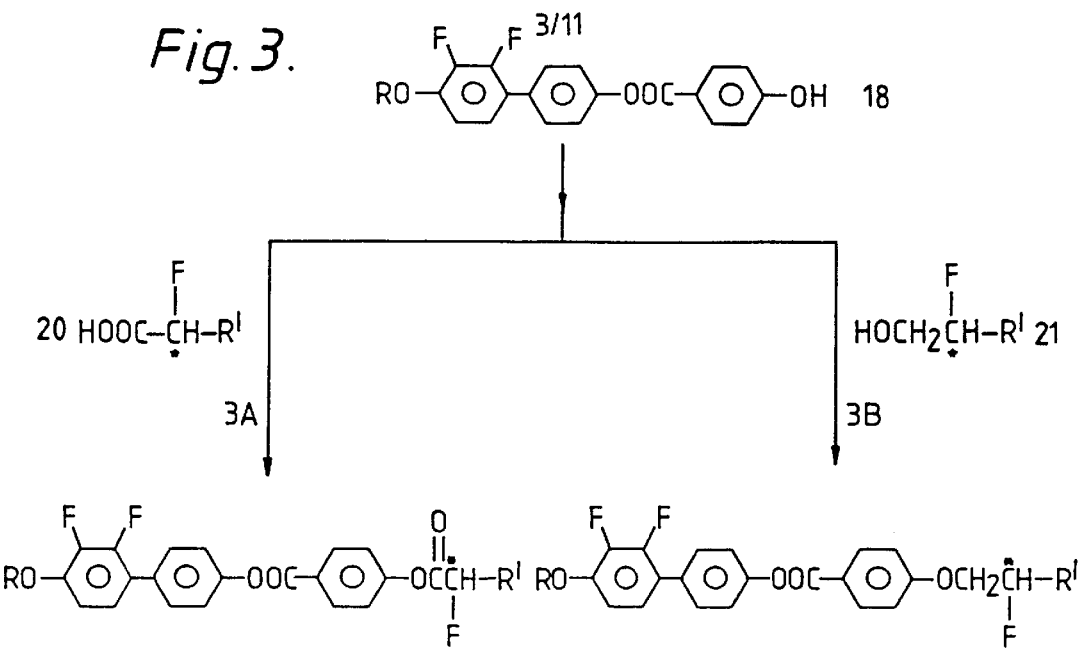
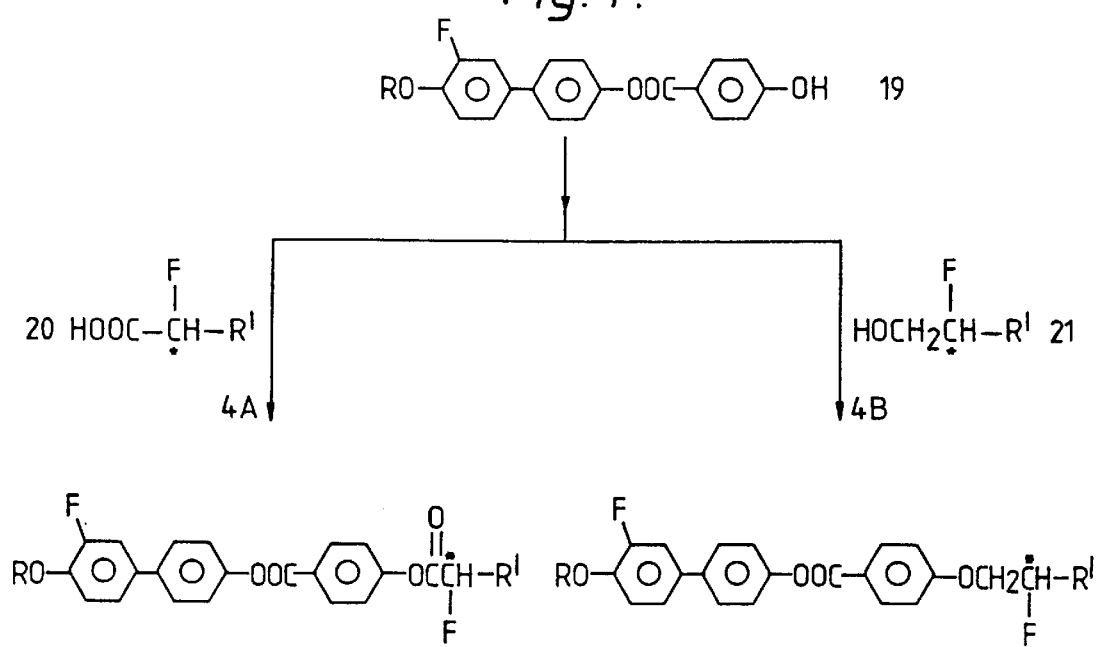

*Fig.6.*
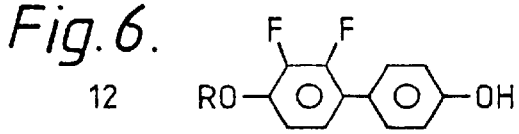
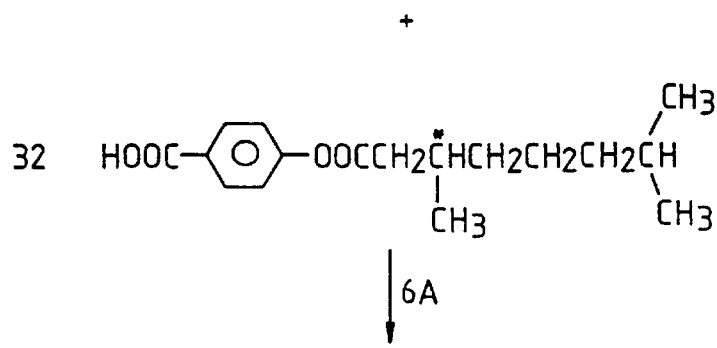
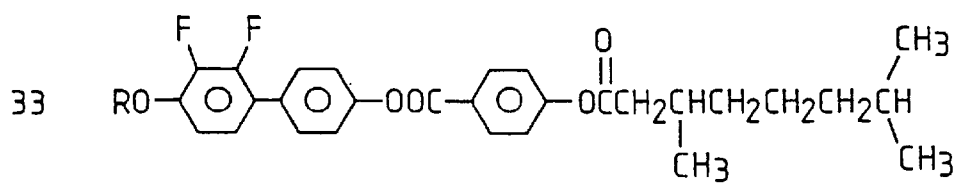
R = C₈H₁₇
*Fig.10.*
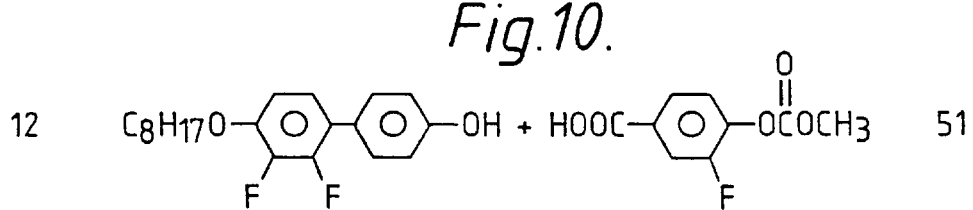
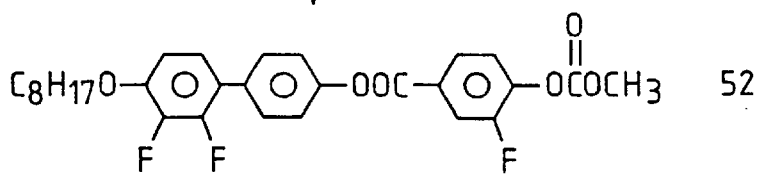
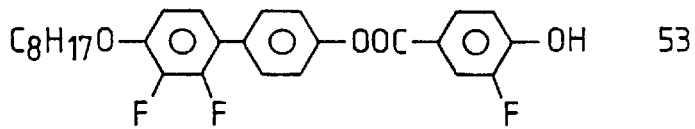

43: X=F, Y=H
41: X=H, Y=F

44: X=F, Y=H
46: X=H, Y=F

43: X=F, Y=H
41: X=H, Y=F

45: X=F, Y=H
47: X=H, Y=F

LIQUID CRYSTAL MATERIALS, MIXTURES AND DEVICES

This application is a 371 of PCT/GB94/01231, filed Jun. 7, 1994.

This invention relates to novel liquid crystal compounds, liquid crystal materials containing them and their inclusion in liquid crystal devices.

Liquid crystals can exist in various phases. In essence there are various classes of liquid-crystalline material, each possessing a characteristic molecular arrangement. For example there are nematic, cholesteric and smectic phases. A wide range of smectic phases exists, for example smectic A and smectic C. Some liquid crystal materials possess a number of liquid crystal phases on varying the temperature, while others have just one phase. For example, a liquid crystal material may show the following phases on being cooled from the isotropic phase: isotropic - nematic - smectic A - smectic C - solid. If a material is described as being smectic A then it means that the material possesses a smectic A phase over a useful working temperature range.

Devices containing ferroelectric liquid crystal mixtures exhibit fast switching times (faster than 100 $\mu$s), Clark and Lagerwall, Appl. Phys. Lett., 36, 89, 1980. They can be bistable which means that they can be multiplexed at high levels using a line-at-a-time fast scan technique. Ferroelectric materials continue to receive a large amount of investigative attention due to their application in high resolution flat panel displays. An important feature of devices containing liquid crystalline materials is that they should exhibit a fast response time. The response time is dependent on a number of factors, one of these being the spontaneous polarisation, denoted Ps (measured in nC cm$^{-2}$). By adding a chiral dopant to the liquid crystalline mixture the value of Ps can be increased, thus decreasing the response time of the device. Ferroelectric smectic liquid crystal materials, which can be produced by mixing an achiral host and a chiral dopant, use the ferroelectric properties of the tilted chiral smectic C, F, G, H, I, J and K phases. The chiral smectic C phase is denoted $S_c^*$ with the asterisk denoting chirality. The $S_C^*$ phase is generally considered to be the most useful as it is the least viscous. It is desirable that the material should exhibit a long pitch nematic (denoted N*) and $S_A^*$ phase at temperatures above the chiral smectic phase in order to assist surface alignment in a device containing liquid-crystalline material. Ferroelectric smectic liquid crystal materials should ideally possess the following characteristics: low viscosity, controllable Ps and an $S_C$ phase that persists over a broad temperature range, which should include ambient temperature, and exhibits chemical and photochemical stability. Materials which possess these characteristics offer the prospect of very fast switching liquid crystal containing devices. Some applications of ferroelectric liquid crystals are described by J.S. Patel and J.W. Goodby in Opt. Eng., 1987, 26, 273.

Other smectic phases exhibit exploitable characteristics. For example the electroclinic effect, first described by S. Garoff and R. Meyer, Phys. Rev. Lett., 38, 848, (1977), usually occurs in the smectic A phase. Unlike ferroelectric devices, the liquid crystal material in electroclinic devices is not bistable. The liquid crystal director within an EC device responds almost linearly to an applied electric field. Electroclinic devices are suitable for various applications including spatial light modulators. UK Patent Application GB 2 244 566 A describes an example of an electroclinic device. Chandani et al., Jpn. J. Appl. Phys., 27, L 729, 1988; Jpn. J. Appl. Phys., 28, L 1261, 1989; Jpn. J. Appl. Phys., 28, L 1265, 1989, first described the antiferroelectric effect which is a tri-stable switching state occurring in a liquid crystal phase designated as SmC$_A^*$. For example, when ferroelectric layers are stacked so that the polarisation vectors in sequential layers oppose one another then an antiferroelectric phase is obtained.

For a review of thermochromism in liquid crystals see J.G. Grabmaier in 'Applications of Liquid Crystals', G. Meier, E. Sackmann and J.G. Grabmaier, Springer-Verlag, Berlin and New York, 1975, pp 83–158.

It is not usual for a single compound to exhibit all of the properties outlined in the preceeding text, hence ferroelectric smectic liquid crystal materials generally consist of a mixture of compounds which when mixed together induce a chiral tilted smectic phase. Some of the compounds which are added to such a mixture are described as additives. Chiral dopants come under the term additive and are added to the liquid crystalline mixture in order to induce the smectic mixture to become chiral smectic and to induce a Ps in the material, or if the material already possesses a Ps then the introduction of a chiral dopant should result in a change of value for Ps. The chiral dopant provides the necessary Ps component required for ferroelectric switching.

The host is generally a material that shows a smectic phase (preferably tilted smectic, especially $S_C$) without being chiral. The dopant is or contains at least one optically active compound, without necessarily showing a smectic phase, although it is preferred if the dopant does itself show a smectic phase. The dopant when mixed with the host results in the mixture becoming chiral and induces a Ps.

Some chiral compounds show smectic phase(s) and are therefore theoretically suitable as both hosts and dopants. This means that it may be possible to have a switchable ferroelectric material made up of a single compound. In practice this is rarely achieved because this type of compound is often very viscous and so has slow response times.

PCT patent application WO 86/00087 describes a series of optically active liquid crystal compounds that contain the chiral groups:

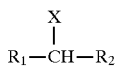

where X represents Cl, CN or CH$_3$ and R$_1$ and R$_2$ represent the residue of the molecule. All of the compounds described necessarily contain the phenyl-pyrimidine group,

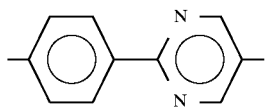

as the mesogenic unit. The pyrimidine ring is said to be particularly beneficial in the short molecules described as its molecular configuration increases intermolecular distances in the bulk, thus reducing the viscosity. Among the many compounds described are:

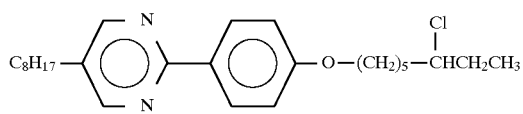

and

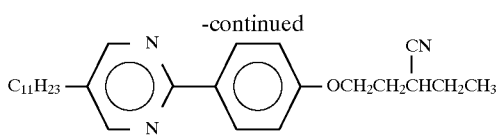

These two compounds do not show smectic phases by themselves.

According to this invention there is provided compounds having a general Formula I Formula I

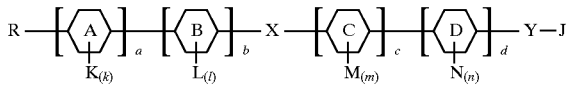

in which R is selected from alkyl, alkoxy or alkenyl and may contain 1–20 carbon atoms; A, B. C, D are independently selected from phenyl, cyclohexyl, pyridyl, pyrimidyl; A may also be dioxanyl, napthyl; b is independently selected from 0, 1 or 2; c is independently selected from 0 or 1; a and d are both equal to 1; K, L, M, N are independently selected from the halogen group; (k), (1), (m), (n), are independently 0, 1, 2, 3, or 4; X is selected from OCO, COO, OCH$_2$, CH$_2$O, CH$_2$CH$_2$; Y is selected from OCO, COO, OOC, OCH$_2$, CH$_2$O, CH$_2$; J is an end group of Formula II which contains a chiral centre

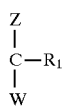

Formula II where Z is selected from halogen, C$_1$—C$_3$ alkyl chain, CN, CF$_3$, CHF$_2$, H; R$_1$ is a linear or branched alkyl group containing 1–15 carbon atoms or H, W is a linear or branched alkyl group containing 1–5 carbon atoms or H; excluding where R is alkoxy, A=B=D=phenyl, K=F, (k)=2, (l)=(n)=0, b=1 c=0, X=OOC, Y=OOC, Z=Cl, R$_1$=CH$_2$CH(CH$_3$)$_2$ W=H;
provided that the total of (k)+(l)+(m)+(n) does not equal 0 and that the total of a+b+c+d is not greater than 4.
Preferably R is C$_{3-12}$ even more preferably C$_{5-9}$.
Preferably A, B, D are phenyl.
Preferably b=1 and c=0.
Preferably K, L, N are independently of each other F or H.
Preferably (k), (1), (n) are independently of one another 0, 1 or 2; even more preferably (k) may be 0, 1 or 2 and (l) and (n) may be independently of each other 0 or 1.
Preferably X is OCO or OCH$_2$ or CH$_2$O; even more preferably X is OCO.
Preferably Y is OOC or OCH$_2$.
Preferably Z is F or C$_{1-3}$ or H; even more preferably Z is F or CH$_3$ or H.
Preferably R$_1$ contains 1–9 carbon atoms or H; even more preferably R$_1$ is C$_{1-6}$ or H. Preferably W is C$_{1-3}$ or H; even more preferably W may contain 1 carbon atom or be H.

The compounds of formula I are further characterised in that they may be used as host materials and dopants. They possess a SC phase therefore measurements on them to deduce, for example Ps, may be done in their pure form.

Compounds of formula I may be used as optically active components of ferroelectric smectic liquid crystal mixtures i.e. as chiral dopants. When used as components of such mixtures compounds of formula I, particularly the preferred compounds referred to above, may offer the following advantages.

i/ They may show a high spontaneous polarisation coefficient (Ps). This may conveniently be expressed in terms of the extrapolated Ps i.e. the Ps of the mixture extrapolated to 100% of the compound of formula I. This means that quite a small amount of the compound of formula I need be included in the mixture.

ii/ They may induce the appearance of chiral smectic phases in the mixture having a very long helical pitch. This may more conveniently be assessed by measuring the chiral nematic N*pitch they induce when mixed with a nematic liquid crystal material. A long pitch is often desirable as in some ferroelectric smectic liquid crystal devices the pitch should be as close as possible to the spacing of the electrodes, and in practice the difficulty of manufacture increases with decreasing electrode spacing.

iii/ Chiral smectic mixtures containing them may show S$_C$*phases which persist over a wide temperature range, including room temperature.

iv/ They are compatible with many hosts and additives for example those discussed below.

v/ They may offer the possibility of very high switching speeds, which is of advantage in for example video screen type applications. This is partly due to i/ above in that many known chiral dopants are viscous and cause mixtures containing them to be viscous. The good Ps induced by compounds of formula I means that relatively little need be used and hence there is little adverse effect on viscosity.

vi/ It is often possible to obtain compounds of formula I in both (R) and (S) enantiomeric forms as both enantiomeric forms of the starting material may be available. This makes the pitch of mixtures containing them particularly easy to 'compensate' (see below) by including opposite-twisting enantiomers of the compounds of formula I in the mixture.

A ferroelectric smectic liquid crystal mixture according to the invention contains at least one compound of formula I. Typically if the compound is present as a dopant the mixture will contain 1–20% by weight of the compound of formula I, eg around 10% or less. Generally the Ps of the mixture is proportional to the amount of chiral dopant present.

The mixture should contain one or more compounds which either separately or together show an Sc phase. Such compounds are known as smectic hosts.

A large number of classes of compounds which may be used as smectic hosts, and some examples of suitable classes are discussed below. Compounds of formula I may be mixed with a wide range of hosts, for example smectic hosts to form a useful liquid crystal composition. Such compositions can have a range of Ps values. Compounds of formula I may be mixed with one or more of the types of hosts VIII-XIII. These different types of hosts may be mixed together to which the compound of general formula I may also may be added.

Typical hosts include:
The compounds described in PCT/GB86/0040, eg of formula VIII

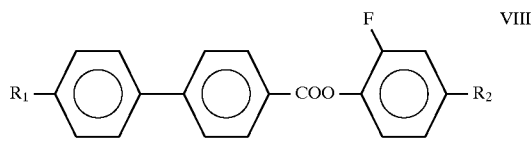

where R$_1$ and R$_2$ are independently C$_3$–C$_{12}$ alkyl or alkoxy.

The fluoro-terphenyls described in EPA 8430494.3 and GBA 8725928, eg of formula IX

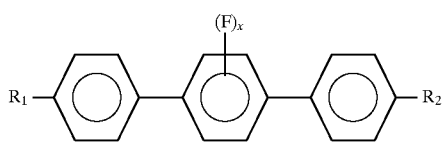

where $R_1$ and $R_2$ are independently $C_3$–$C_{12}$ alkyl or alkoxy, x is 1 and F may be on any of the available substitution positions on the phenyl ring specified.

The difluoro-terphenyls described in GBA 8905422.5, eg of formula X

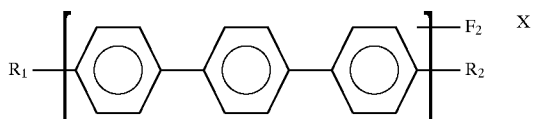

where $R_1$ and $R_2$ are independently $C_3$—$C_{12}$ alkyl or alkoxy.

The phenyl-pyrimidines described in WO 86/00087, eg of formula XI

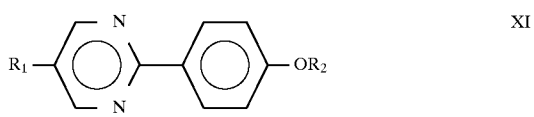

including those compounds where $R_1$ is $C_3$–$C_{12}$ alkyl and $R_2$ is given by the general formula $(CH_2)_n$—$CHXCH_2CH_3$, where n is 1 to 5 and X is CN or Cl.

The compounds described by R. Eidenschink et. at. in Cyclohexanederivative mit Getilteneten Smektischen Phasen at the $16_{th}$ Freiberg Liquid Crystal Conference, Freiberg, Germany, p8. Available from E. Merck Ltd., Germany, eg of formula XII.

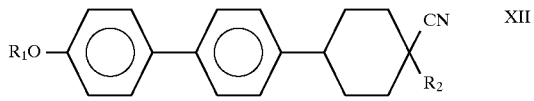

including those compounds where $R_1$ and $R_2$ are independently $C_1$–$C_{15}$ alkyl.

The difluoro-phenyl pyrimidines described at the $_2$nd International Symposium on Ferroelectric Liquid Crystals, Göbteborg, Sweden, June 1989 by Reiffenrath et. al., eg of formula XIII

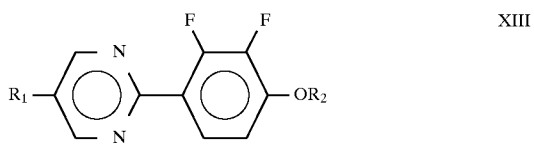

including those compounds where $R_1$ and $R_2$ are independently $C_3$—$C_9$ alkyl.

These hosts allow the possibility of sc mixtures showing an SC phase persisting over a wide temperature range including room temperature, and also an SA phase at a temperature above the SC, to assist in the alignment of the liquid crystal material.

The compounds of formula I may also may be used as host materials.

Additives in such a mixture may serve a number of functions. One such function is as pitch compensators. Pitch compensation is the inclusion in the ferroelectric smectic mixture of two or more compounds which induce the appearance of helical smectic phases of opposite twist sense. In such a case the compounds will unwind the helical phase induced by the other. This may be used to produce a long pitch helical smectic phase, and by the controlled use of appropriate quantities of the two compounds the pitch of the mixture may be closely controlled.

In mixtures according to the invention, pitch compensation may be achieved conveniently by using opposite-twisting compounds of formula I or by using different compounds from formula I.

The compounds of formula I may be advantageously used in ferroelectric liquid crystal displays, electroclinic displays and as long pitch materials.

The intention will now be described by way of example only with reference to the accompanying drawings of which:

FIG. 1 describes a synthetic route for the preparation of compounds 3–13.

FIG. 2 describes a synthetic route for the preparation of compounds 15–19.

FIG. 3 describes a synthetic route for the preparation of compounds 22–23.

FIG. 4 describes a synthetic route for the preparation of compounds 24–25.

FIG. 5 describes a synthetic route for the preparation of compounds 27–31.

FIG. 6 describes a synthetic route for the preparation of compounds 33.

FIG. 7 describes a synthetic route for the preparation of compounds 3614 38, 40–43.

FIG. 8 describes a synthetic route for the preparation of compounds 44 and 46.

FIG. 9 describes a synthetic route for the preparation of compounds 45 and 47.

FIG. 10 describes a synthetic route for the preparation of compounds 52–53.

FIG. 11 describes a synthetic route for the preparation of compound 48.

FIG. 12 describes a synthetic route for the preparation of compound 49.

FIG. 13 describes a synthetic route for the preparation of compounds 50, 54 and 55.

Figure 1:
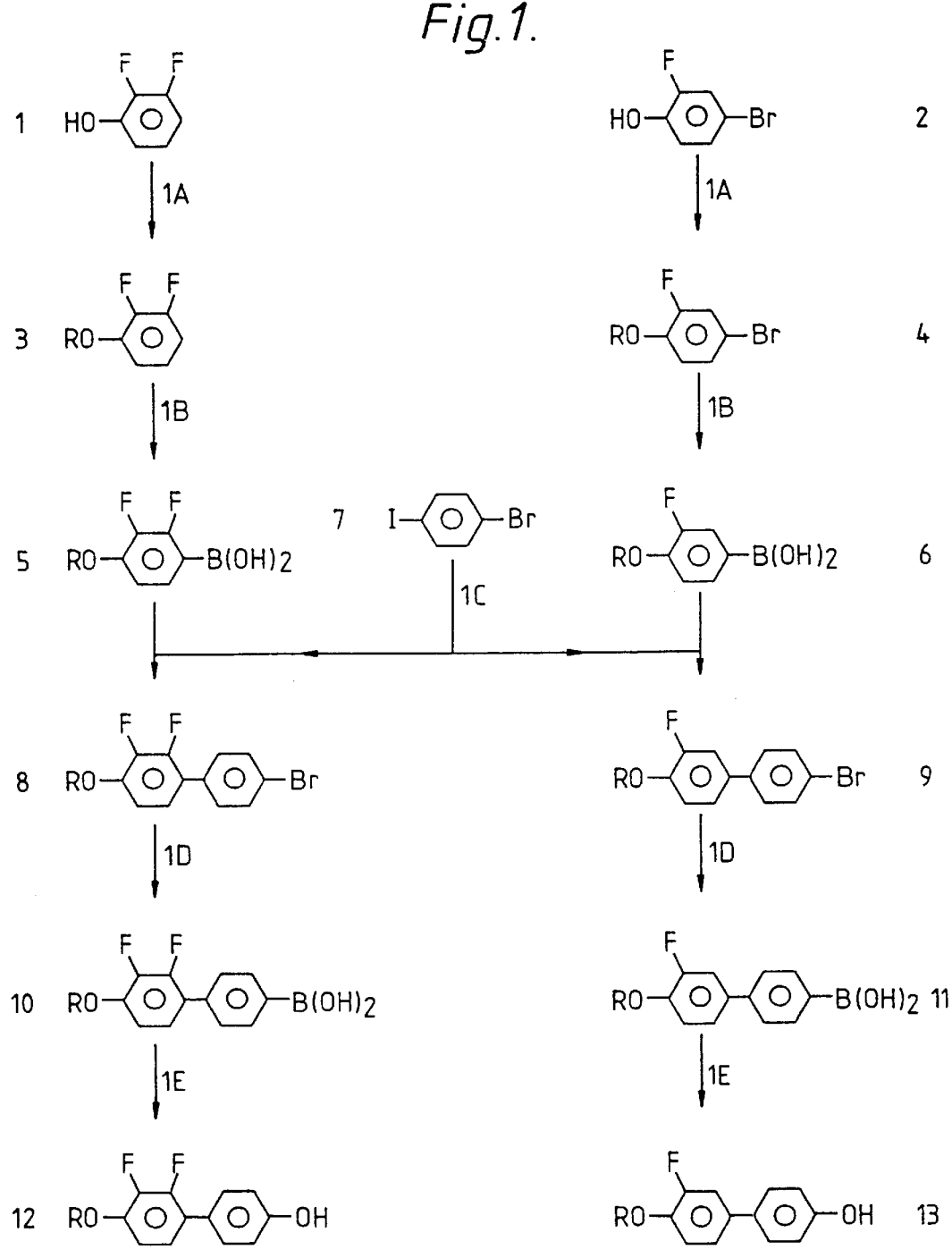
Figure 2:
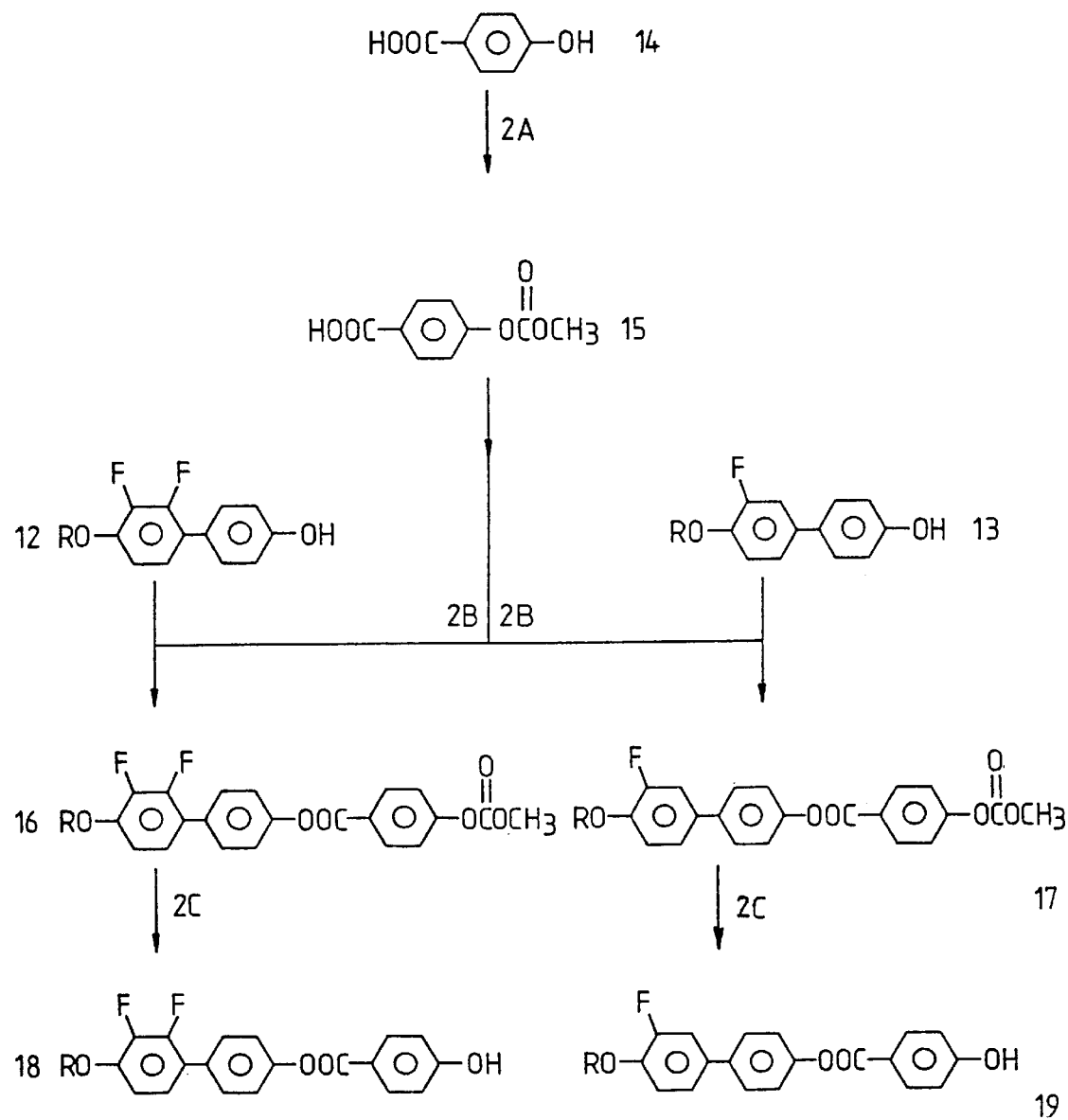
Figure 5:
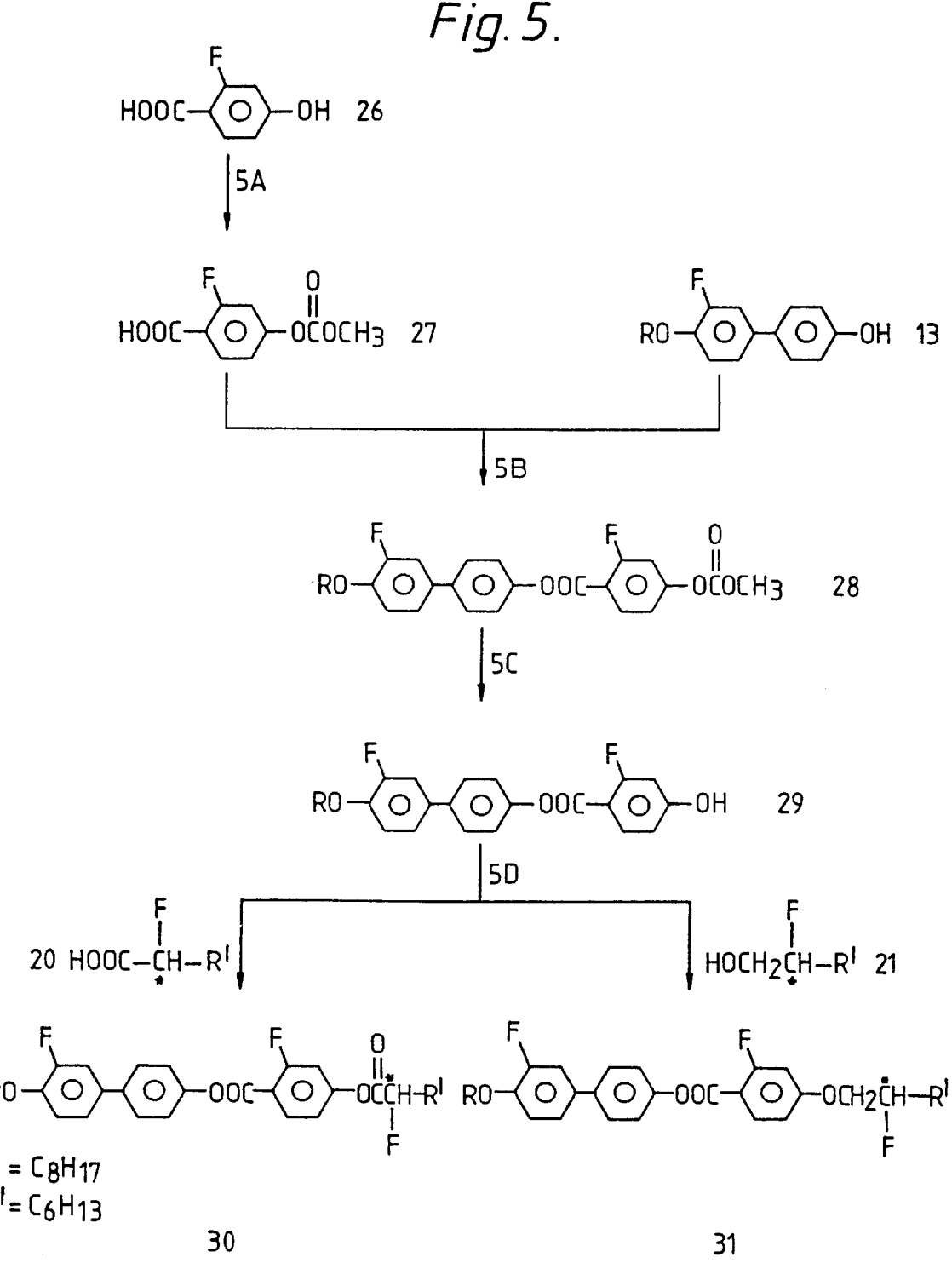
Figure 7:
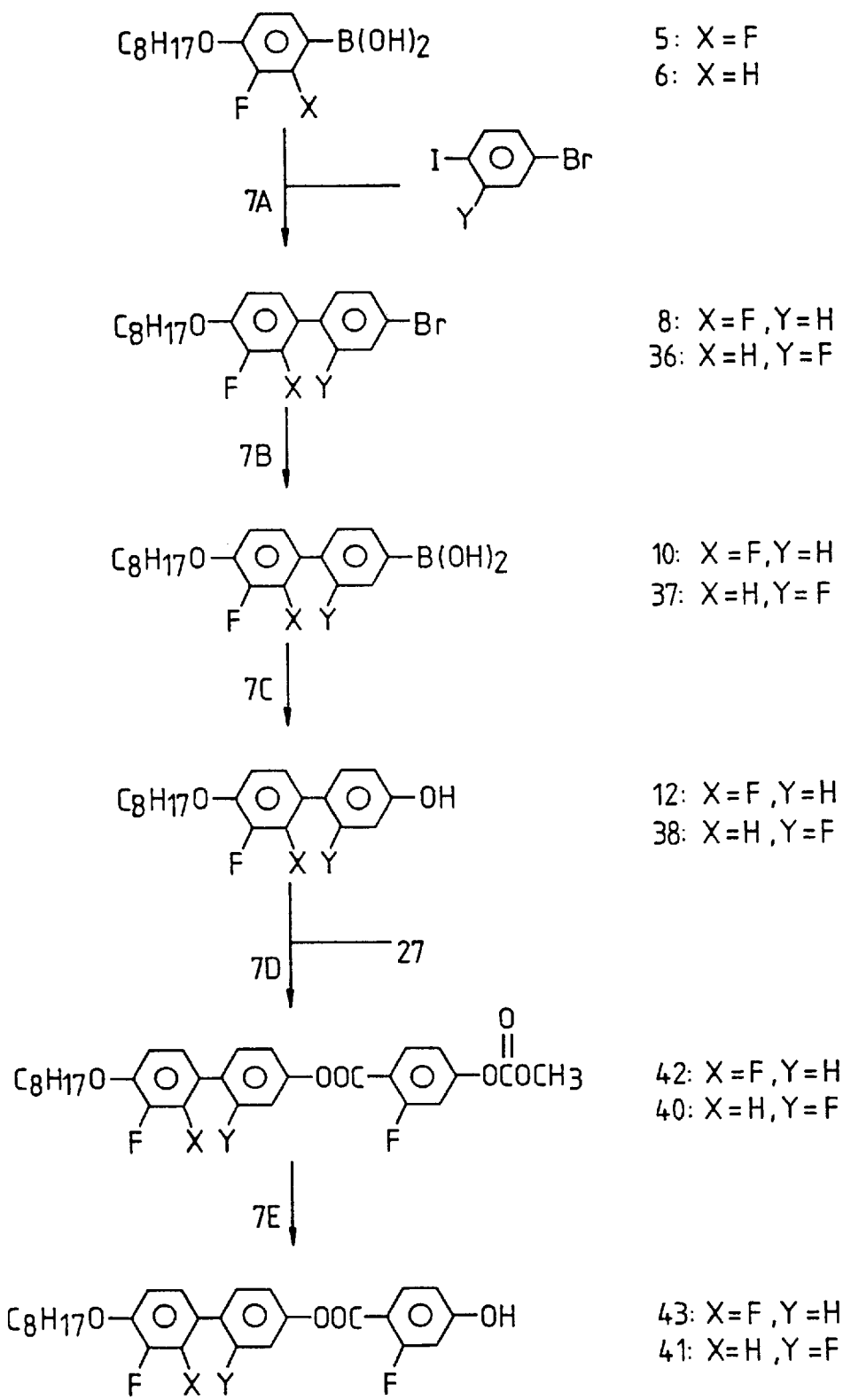
Figure 8:
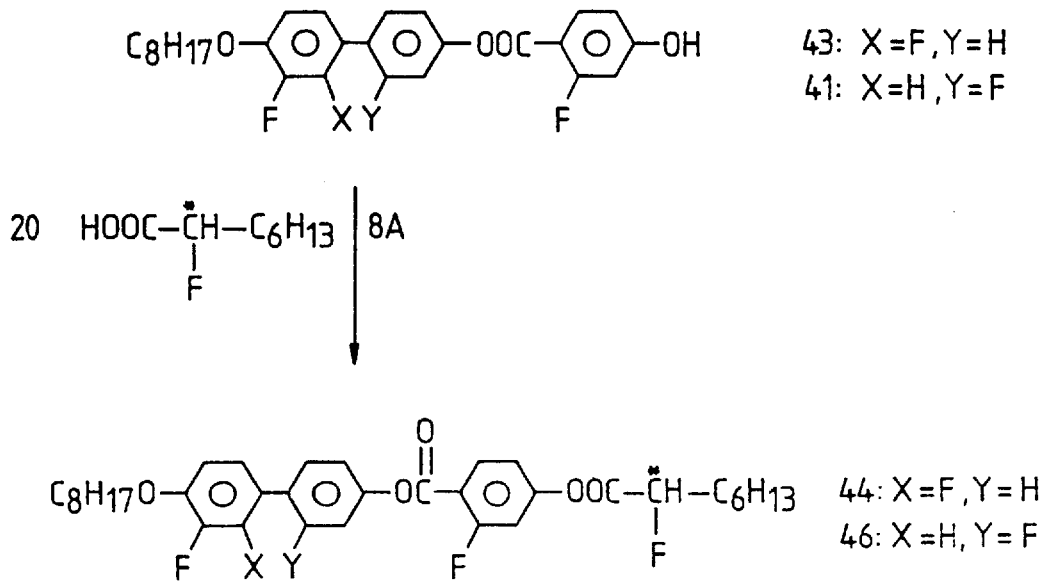
Figure 9:
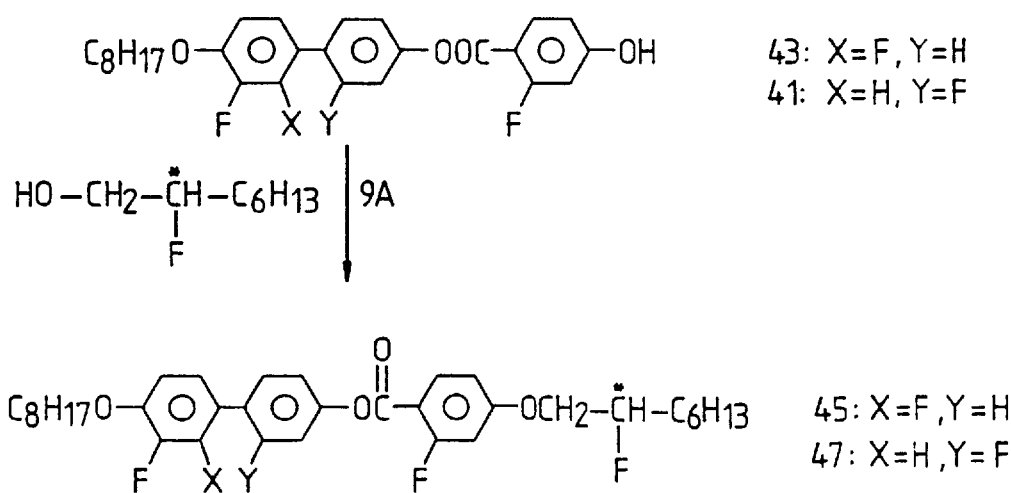
Figure 11:
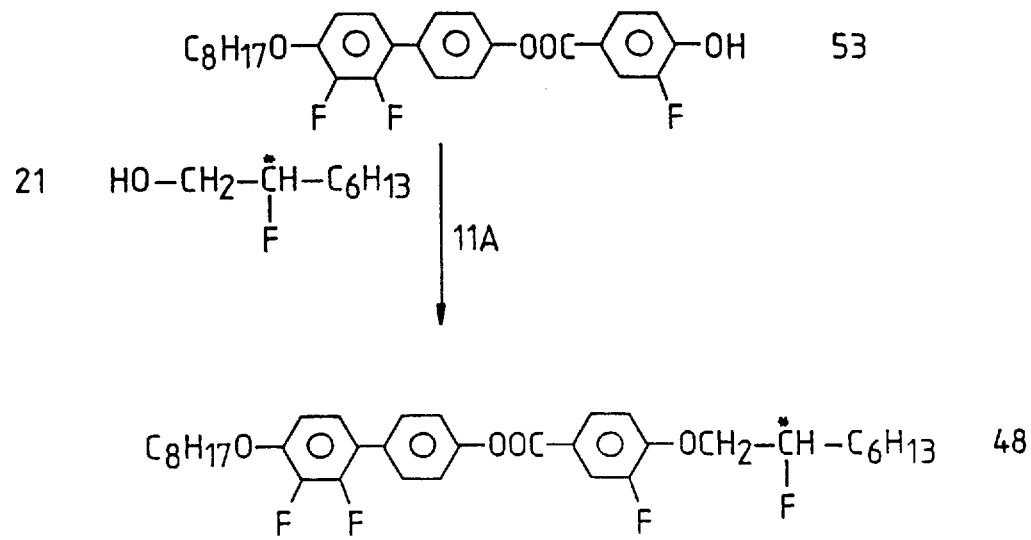
Figure 12:
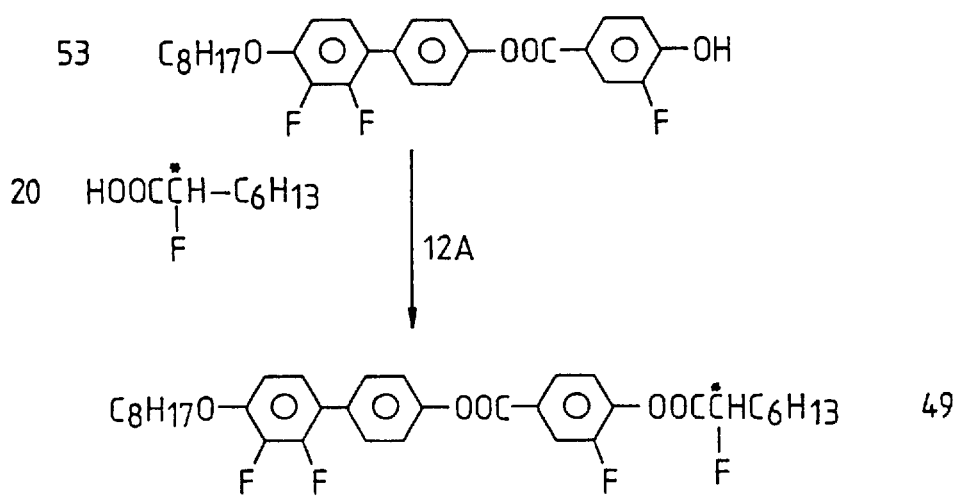
Figure 13:
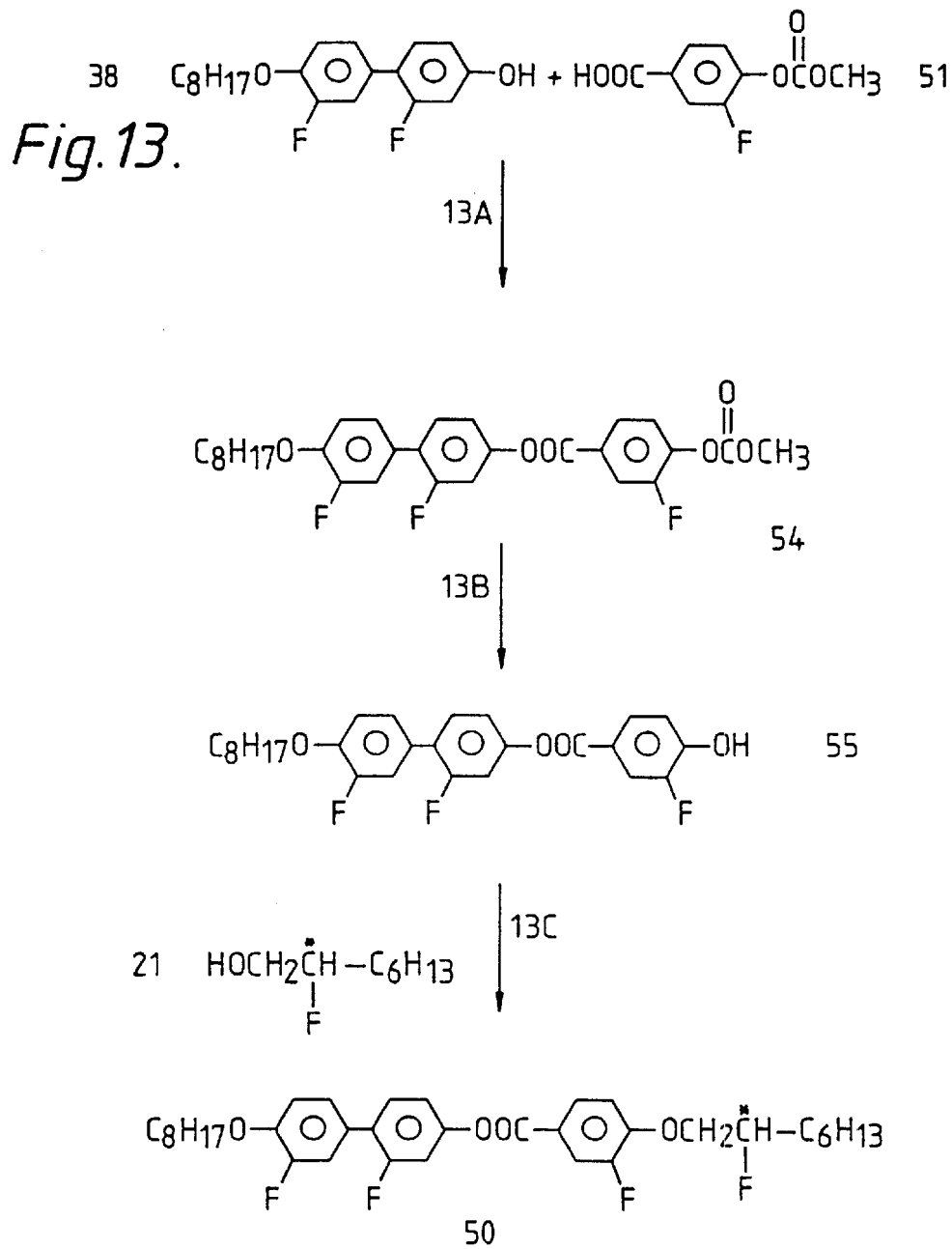

Reagents used in the synthetic route of FIGS. 1–13 are shown in the corresponding Schemes 1–13.

Difluorophenol (1) and 1-bromo-3-fluorophenol (2) were purchased from Fluorochem Ltd.

2-fluoro-4-hydroxybenzoic acid was obtained from Merck Ltd.

(S)-2-fluoro-octanoic acid (20) and (S)-2-fluoro-octanol (21) were obtained from E. Merck.

(S)-4-(2,6-dimethylheptylcarbonyloxy)benzoic acid (32) is a standard intermediate.

Scheme 1

1A: $K_2CO_3$, RBr, acetone
1B: (i) n-BuLi, [($^i$PrO)$_3$B], THF; (ii) 10% HCl
1C: [Pd(PPh$_3$)$_4$], DME, 2M Na$_2$CO$_3$
1D: (i) n-BuLi, [($^i$PrO)$_3$B], THF; (ii) 10% HCl
1E: 10% $H_2O_2$, Et$_2$O.

-continued

Scheme 2

2A: CH$_3$OCOCl, NaOH, H$_2$O
2B: DEAD, PPh$_3$, THF
2C: 35% NH$_3$, EtOH.

Scheme 3

3A: DCC, DMAP, CH$_2$Cl$_2$
3B: DEAD, PPh$_3$, THF.

Scheme 4

4A: DCC, DMAP, CH$_2$Cl$_2$
4B: DEAD, PPh$_3$, THF.

Scheme 5

5A: CH$_3$OCOCl, NaOH, H$_2$O
5B: DEAD, PPh$_3$, THF
5C: 35% NH$_3$, EtOH
5D: DCC, DMAP, CH$_2$Cl$_2$.

Scheme 6

6A: DCC, DMAP, CH$_2$Cl$_2$.

Scheme 7

7A: [Pd(PPh$_3$)]$_4$, DME, 2M Na$_2$CO$_3$
7B: (i) n-BuLi, [($^i$PrO)$_3$B], THF; (ii) 10% HCl
7C: 10% H$_2$O$_2$, Et$_2$O.
7D: DEAD, PPh$_3$, THF
7E: 35% NH$_3$, EtOH.

Scheme 8

8A: DCC, DMAP, CH$_2$Cl$_2$.

Scheme 9

9A: DEAD, PPh$_3$, THF

Scheme 10

10A: DEAD, PPh$_3$, THF
10B: 35% NH$_3$, EtOH.

Scheme 11

11A: DEAD, PPh$_3$, THF

Scheme 12

12A: DCC, DMAP, CH$_2$Cl$_2$.

Scheme 13

13A: DEAD, PPh$_3$, THF
13B: 35% NH$_3$, EtOH.
13C: DEAD, PPh$_3$, THF

Abbreviations for schemes.
DME: dimethoxyethane, DEAD: diethylazodicarboxylate,
DCC: dicyclohexylcarbodiimide, DMAP: N,N-dimethylaminopyridine.

Compound 3:
1,2-difluoro-3-octoxybenzene

A solution of 1-bromo-octane (25.1g, 0.13mol) in acetone (30ml) was added to a stirred, refluxing mixture of 2,3-difluorophenol (1) (14g, 0.108mol) and potassium carbonate (20.0g, 0.144mol) in acetone (300ml). The stirred mixture was heated under reflux for 24hr (or until the analysis revealed a complete reaction). The potassium carbonate was filtered off and most of the acetone removed in vacuo. The residue was dissolved in ether, water was added and the layers separated. This was followed by a second extraction of the aqueous layer with ether. The combined organic layers were washed with water, 5% sodium hydroxide, water and dried (MgSO4). The solvent was removed under vacuum. The crude product was distilled to give a colourless oil.
Yield=17.1 g, (65%)
bp=78°–81° C. (0.4Nm$^{-2}$)

Compound 4:
1-bromo-3-fluoro-4-octoxybenzene

This was prepared using a similar method to that described for compound 3. The crude product was distilled. Quantities: 4-bromo-3-fluorophenol (10.0 g, 0.052 mol), 1-bromo-octane (12.0 g, 0.062 mol), potassium carbonate (14.5g, 0.105mol).
Yield=11.16 g (71%)
bp 112°–114° C. (1.3Nm $^{-2}$)

Compound 5:
2, 3-difluoro-4-octoxyphenylboronic acid

A solution of 1,2-difluoro-4-octoxybenzene (6.74g, 0.029 mol) (3), in dry THF (100 ml) was cooled to −78° C. and n-butyllithium (3.2ml, 10M in hexane, 0.032mol) was added dropwise. The reaction mixture was maintained under these conditions for 2.5hr and then a solution of tri-isopropylborate (10.91 g, 0.058 mol) in dry THF (30 ml) was added dropwise at −78° C. The reaction mixture was allowed to warm to room temperature overnight and then stirred for 1 h with 10% HCl (30ml). The product was extracted into ether (twice), and the combined ethereal extracts were washed with water and dried (MgSO$_4$). The solvent was removed in vacuo to give a colourless solid.
Yield=8.21 g, (98%)

Compound 6:
3-fluoro-4-octoxyphenylboronic acid

This was prepared using a similar method to that described for compound 5. Quantities: 1-bromo-3-fluoro-4-octoxybenzene (15 g, 0.05 mol), n-butyllithium (5 ml, 10M in hexane, 0.05 mol), tri-isopropylborate (18.81 g, 0.1 mol).
Yield =7.5g, (56%).

Compound 8:
4'-bromo-2.3-difluoro-4-octoxybiphenyl

A solution of 2,3-difluro-4-octoxyphenylboronic acid (5) (8.29 g, 0.029 mol) in dimethoxyethane (40 ml) was added to a solution of 4-bromoiodobenzene (6.80 g, 0.024 mol) and tetrakis(triphenylphosphine)palladium (0) (1.$^4$8 g. 1.29 mmol) in dimethoxyethane (40 ml) under nitrogen. To this, 2M sodium carbonate (60 ml) was added. The stirred mixture was refluxed gently. Progress of the reaction was carefully monitored using tlc until the 4-bromoiodobenzene had reacted completely (usually 4–5hr). The layers were separated and the aqueous layer once more extracted with ether. The combined organic layers were washed with brine and dried (MgSO$_4$). The solvent was removed in vacuo and the residue purified by column chromatography (silica gel/ petroleum fraction (bp 40°–60° C.) - ethyl acetate, 9:1) to give a white solid which was recrystallised from pentane (−20° C.) to yield colourless crystals.
Yield=5.28 g. (61%)
mp 39 °–40° C.

Compound 9:
4'-bromo-3-fluoro-4-octoxybiphenyl

This was prepared using a similar method to that described for compound 8. Quantities: 3-fluoro-4-octoxyphenyl boronic acid (7.0 g, 0.026 mol), 4-bromoiodobenzene (5.88 g, 0.021 mol), tetrakis (triphenylphosphine)palladium (0) (0.8 g, 0.7 mol).
Yield=5.09g, (64%)
mp=42°–44° C.

Compound 10:
2,3-difluoro-4-octoxybiphenyl-4'-yl-boronic acid

This was prepared using a similar method to that described for compound 5. Quantities: 4'-bromo-2,3- difluoro-4-octoxybiphenyl (8) (3.18g, 8.0 mmol), n-butyllithium (3.2 ml, 2.5M/hexane, 8.0 mmol), tri-isopropylborate (3.01 g, 16.0 mmol).
Yield=2.9 g, (100%).

Compound 11:
3-fluoro-4-octoxybiphenyl-4'-yl-boronic acid
This was prepared using a similar method to that described for compound 5. Quantities: 4'bromo-3-fluoro-4-octoxybiphenyl (4.95 g, 0.013 mol), n-butyllithium (5 ml, 2.5M/hexane, 0.013 mol), tri-isopropylborate (4.7 g, 0.026 mol).
Yield =4.40 g, (98%)

Compound 12:
2,3-difluoro-4-octoxy-4'-hydroxybiphenyl
10% hydrogen peroxide (10.5 ml, 0.023 mol) was added dropwise to a stirred, refluxing solution of 2,3-difluoro-4-octoxybiphenyl-4'-yl-boronic acid (10) (2.9g, 8.0 mmol), in diethyl ether (40 ml). The stirred mixture was heated under reflux until tic showed the reaction to be complete. The ether layer was separated and the aqueous layer extracted with ether. The combined ethereal layers were washed with water and dried. The solvent was removed. The crude product was purified by flash chromatography (silica gel/petroleum fraction (bp 40°–60° C.) - ethyl acetate, 2:1) to give a white solid which was recrystallised from pentane/ethyl acetate mixtures.
Yield=2.1 g, (78%),
mp=112.5°–113.5° C.

Compound 13:
3-fluoro-4-octoxy-4'-hydroxybiphenyl.
This was prepared using a similar method to that described for compound 12. Quantities: 3-fluoro-4-octoxybiphenyl-4'-yl-boronic acid (11) (4.40 g, 0.012 mol), 10% hydrogen peroxide (16 ml, 0.036 mol).
Yield=3.78 g, (72%),
mp=126°–28° C.

Compound 15:
4-methoxycarbonyloxybenzoic acid
A solution of sodium hydroxide (15 g) in water (400 ml) was chilled to 0° C. in ice. To this the 4-hydroxy benzoic acid (17.9 g, 0.130 mol) was added. Methylchloroformate (20 g, 0.212 mol) was added slowly to prevent the temperature from rising above 5° C. The reaction mixture was stirred at 0°–5° C. for 3 h during which time a white suspension gradually formed. The pH was adjusted to 4-5 with addition of HCl/water (1:1). The voluminous precipitate was filtered off, washed with water and recrystallised from ethanol (200 ml).
Yield=23.2g. (91%). mp=177°–178° C.

Compound 16:
2,3-difluoro-4-octoxybiphenyl-4'-yl 4-methoxycarbonyloxybenzoate.
To a solution of 4-methoxycarbonyloxybenzoic acid (1.50 g, 7.64 mmol) (15) and 2,3 -difluoro-4-octoxy-4'-hydroxybiphenyl (12) (2.55 g, 7.64 mmol) in THF (60 ml) was added diethylazodicarboxylate (1.329 g, 7.64 mmol) under an atmosphere of dry nitrogen. Triphenylphosphine (2.003 g, 7.64 mmol), dissolved in dry THF (60 ml) was added slowly to the resulting stirred solution. The solution was stirred for 8 h at room temperature when the solvent was removed under reduced pressure to give an off-white solid. The product was purified by flash chromatography (silica gel/petroleum fraction (bp 40°–60° C.) - dichloromethane, 1:2).
Yield=3.05 g, (78%)
Phase Transitions (°C) K 76.0/99.8N 201.9 I
Between the K(crystalline) and N(nematic) phases the first temperature is the point of crystallisation and the second temperature is the melting point.

Compound 17:
3-fluoro-4-octoxybiphenyl-4'-yl 4-methoxycarbonyloxybenzoate
This was prepared using a similar method to that described for compound 16. Quantities: 4-methoxycarbonyloxybenzoic acid (15) (0.74 g, 3.79 mmol), triphenylphosphine (0.995g, 3.79mmol). Yield=1.3 g, (69%)
Phase Transitions (°C.) K 88.1/112.0N 216.2 I
Between the K(crystalline) and N(nematic) phases the first temperature is the point of crystallisation and the second temperature is the melting point.

Compound 18:
2,3-difluoro-4-octoxybiphenyl-4'-yl 4-hydroxybenzoate.
A suspension of 2,3-difluoro-4-octoxybiphenyl-4'-yl 4-methoxycarbonyloxybenzoate (2.7 g, 5.27 mmol) (16) was stirred in a mixture of ethanol (60 ml) and ammonia (60 ml, 35%) at room temperature for 8 h or until the conversion was shown to be complete. The volatile components were removed in vacuo (<55° C.) to give a white powder which was further dried in vacuo.
Yield=2.34 g, (97%)
mp=145° C.

Compound 19:
3-fluoro-4-octoxybiphenyl-4'-yl 4-hydroxybenzoate
This was prepared using a similar method to that described for compound 18 and the product was recrystallised twice from ethyl acetate/hexane mixtures. Quantities: 3-fluoro-4-octoxybiphenyl-4'-yl 4-methoxycarbonyloxybenzoate (1.3 g, 2.63 mmol).
Yield=0.91 g, (79%).

Compound 22:
2,3-difluoro-4-octoxybiphenyl-4'-yl 4-((S)-2-fluorooctanoyloxy)benzoate.
To a solution of 2.3-difluoro-4-octoxybiphenyl-4'-yl 4-hydroxybenzoate (18) (0.5 g, 1.1 mmol), (S)-2-fluorooctanoic acid (20) (0.178 g, 1.1 mmol) and N,N-dimethylaminopyridine [DMAP] (0.03 g) in dry dichloromethane (25 ml) was added dropwise, but quickly, a solution of dicyclohexylcarbodiimide (0.25 g, 1.2 mmol) in dry dichloromethane (25 ml) under dry nitrogen. The reaction mixture was stirred at room temperature for 3h. The dicyclohexylurea precipitate was removed by filtration and the solvent removed under reduced pressure. The product was purified by flash chromatography (silica gel/petroleum fraction (bp 40–60)-dichloromethane, 1:2 initially, but gradually increasing the polarity to 1:9).
Yield=0.39 g (59%).

Compound 23:
2,3-difluro-4-octoxybiphenyl-4'-yl 4-((S)-2-fluorooctyloxy)benzoate.
This was prepared using a similar method to that described for compound 16. Quantities: (S)-2-fluorooctanol (21) (0.16 3g, 1.1 mmol), 2,3-difluoro-4-octoxybiphenyl-4'-yl 4-hydroxybenzoate (0.50 g, 1.1 mmol) (18), diethylazodicarboxylate (0.192g, 1.1 mmol), triphenylphosphine (0.29 g, 1.1 mmol). Yield=0.31 g, (48%).

Compound 24:
3-fluoro-4-octoxybiphenyl-4'-yl 4-((S)-2-fluorooctanoyloxy)benzoate.
This was prepared using a similar method to that described for compound 22. Quantities: (S)-2-fluorooctanoic acid (20) (0.165 g, 1.0 mmol), 3-fluoro-4-octoxybiphenyl-4'-yl 4-hydroxybenzoate (19) (0.445 g, 1.0 mmol), dicyclohexylcarbodiimide (0.232 g, 1.0 mmol), N,N-dimethylaminopyridine (0.03 g).

Yield=0.43 g (73%).
Compound 25:
3-fluoro-4-octoxybiphenyl-4'-yl 4-((S)-2-fluorooctyloxy)benzoate.

This was prepared using a similar method as for compound 16. Quantities: (S)-2-fluorooctanol (21) (0.153 g, 1.03 mmol), 3-fluoro-4-octoxybiphenyl-4'-yl 4-hydroxybenzoate (0.450 g, 1.03 mmol), diethylazodicarboxylate (0.179 g, 1.03 mmol), triphenylphosphine (0.270 g, 1.03 mmol).
Yield=0.25g9 (43%).
Compound 27:
2-fluoro-4-methoxycarbonyloxybenzoic acid.

This was prepared using a similar method to that described for compound 15. Quantities: 2-fluoro-4-hydroxybenzoic acid (26) (0.97 g, 6.23 mmol), methylchloroformate (1.09 g, 11.48 mmol).
Yield=1.5 g, (89%).
mp =165°–166° C.
Compound 28:
3-fluoro-4-octoxybiphenyl-4'-yl 2-fluoro-4-methoxycarbonyloxybenzoate.

This was prepared using a similar method to that described for compound 16. Quantities: 2-fluoro-4-methoxycarbonyloxybenzoic acid (27) (0.86 g. 4.0 mmol), 3-fluoro-4-octoxy-4'-hydroxybiphenyl (13), diethylazodicarboxylate (0.7 g, 4.0 mmol)triphenylphosphine (1.05 g, 4.0 mmol).
Yield=1.10 g, (53%).
Phase Transitions (°C.) K 62.0/86.2N 192.1 I
Compound 29:
3-fluoro-4-octoxybiphenyl-4'-yl 2-fluoro-4-hydroxybenzoate This was prepared using a similar method to that described for compound 18.
Quantities:
b 3-fluoro-4-octoxybiphenyl-4'-yl 2-fluoro-4-methoxycarbonyloxybenzoate (28) (1.0 g, 2.0 mmol).
Yield=0.88 g, (99%).
Compound 30:
3-fluoro-4-octoxybiphenyl-4'-yl 2-fluoro-4-((S)-2-fluorooctanoyloxy) benzoate.

This was prepared using a similar method to that described for compound 22. Quantities: (S)-2-fluorooctanoic acid (20) (0.178 g, 1.1 mmol), 3-fluoro-4-octoxybiphenyl-4'-yl 2- fluoro-4-hydroxybenzoate (29) (0.$^4$98 g, 1.1 mmol), dicyclohexylcarbodiimide (0.248 g, 1.2 mmol), N,N-dimethylaminopyridine (0.03 g).
Yield=0.50 g, (76%).
Compound 31:
3-fluoro-4-octoxybiphenyl-4'-yl 2-fluoro-4-((S)-2-fluorooctyloxy)benzoate.

This was prepared using a similar method to that described for compound 16. Quantities: (S)-2-fluoro-octanol (21) (0.147 g, 1.0 mmol), 3-fluoro-4-octoxybiphenyl-4'-yl 2-fluoro-4-hydroxybenzoate (29), diethylazodicarboxylate (0.172 g, 1.0 mmol), triphenylphosphine (0.260 g, 1.0 mmol).
Yield0.35 g, (60%).
Compound 33:
2,3-difluoro-4-octoxybiphenyl-4'-yl 4-((S)-3,7-dimethyloctanoyloxy)benzoate.

This was prepared using a similar method to that described for compound 22. Quantities: 4-((S)-2,6-dimethylheptylcarbonyloxy)benzoic acid (32) (0.320g, 1.1 mmol, 2,3-difluoro-4-octoxy-4'-hydroxybiphenyl (12) (0.366 g, 1.1 mmol), dicyclohexylcarbodiimide (0.250 g, 1.21 mmol), N,N-dimethylaminopyridine (0.04g).

Yield=0.48 g, (71%).
Compound 36:
3-fluoro-4-octoxy-4'-bromo-2'-fluorobiphenyl.

This was prepared using a similar method to that described for compound 8. The product is a low melting solid and was used without further purification. Quantities: 3-fluoro-4-octyloxyphenylboronic acid (6) (6.83 g, 0.026 mol), 1-bromo-3-fluoro-4-iodobenzene (6.92 g, 0.023 mol), tetrakis(triphenylphosphine)palladium(0) (1 g, 0.87 mmol).
Yield=4.27 g, (47%).
Compound 37:
3-fluoro-4-octoxy-2'-fluorobiphenyl-4'-yl boronic acid.

This was prepared using a similar method to that described for compound 11. Quantities: Compound 36 (4.25 g, 0.011 mol), n-butyllithium (4. 5ml, 2.5M in hexane, 0.011 mol), trimethylborate (2.22g. 0.021mol).
Yield=2.5 g, (51%).
Compound 38:
2'3-difluoro-4'-hydroxy-4-octoxybiphenyl.

This was prepared using a similar method to that described for compound 12. The crude product was recrystallised from hexane to give colourless needles. Quantities: compound 37 (2.5 g, 5.5 mmol), hydrogen peroxide (10%, 15 ml, 0.044 mol).
Yield=1.54 g, (67%),
mp=82°–83° C.
Compound 40:
2',3-difluoro-4-octoxybiphenyl-4'-yl 2-fluoro-4-methoxycarbonyloxybenzoate.

This was prepared using a similar method to that described for compound 16. The crude product was purified by flash chromatography (silica gel; petroleum ether/dichloromethane 1:2) to give a white solid. Quantities: compound 38 (0.70 g, 2.09 mmol), 2-fluoro-4-methoxycarbonyloxybenzoic acid (0.448 g, 2.09 mmol), diethylazodicarboxylate (0.438 g, 2.51 mmol), triphenylphosphine (0.659 g, 2.51 mmol).
Yield=0.78 g, (70%).
Phase Transitions (°C.) K 54.3/79.0N 174.0 I
Compound 41:
2',3-difluoro-4-octyloxybiphenyl-4'-yl 2-fluoro-4-hydroxybenzoate.

A solution of compound 40 (0.610 g, 1.15 mmol) in 20ml dichloromethane and 20 ml ethanol was added to 35% ammonia (20 ml) at room temperature. The mixture was stirred for 4 h or until tlc indicated the reaction to be complete. The solvents were removed in vacuo and the residue purified by column chromatography (silica gel; petroleum ether/ethylacetate 2:1). The product was further purified by recrystallisation from ethyl acetate/hexane mixtures to give white crystals.
Yield=0.33 g, (61%),
mp=169°–170° C.
Compound 42:
2,3-difluoro-4-octyloxybiphenyl-4'-yl 2-fluoro-4-methoxycarbonyloxybenzoate.

This was prepared using a similar method to that described for compound 40. Quantities: compound 12 (1.40 g, 4.2 mmol), 2-fluoro-4-methoxycarbonyloxybenzoic acid (0.897 g, 4.2 mmol), diethylazodicarboxylate (0.875 g, 5.0 mmol), triphenylphosphine (1.318 g, 5.0 mmol).
Yield=1.10 g, (49%).
Phase Transitions (°C.) K 60.5/117.3N 164.7 I
Compound 43:
2,3-difluoro-4-octyloxybiphenyl-4'-yl 2-fluoro-4-hydroxybenzoate This was prepared using a similar method to that described for compound 41. The product was recrystallised from ethyl acetate/hexane mixtures to give fine colourless needles. Quantities: compound 42 (1.00 g, 1.9 mmol), ammonia (10–35%., 30 ml).
Yield =0.58g, (64%),
mp =179-180° C.
Compound 44:
2,3-difluoro-$^4$-octyloxybiphenyl-4'-yl
2-fluoro-4-((S)-$^2$-fluorooctanoyloxy)benzoate.

To a solution of compound 43 (0.160 g, 0.30 mmol), (S)-2-fluorooctanoic acid (0.055 g, 0.30 mmol) and dimethylaminopyridine (0.011 g) in dry dichloromethane (20 ml) under nitrogen was added a solution of dicyclohexylcarbodiimide (0.084 g, 0.40 mmol) in dichloromethane (5 ml). The reaction mixture was stirred at room temperature for 8 h after which the DCU formed was removed by filtration and the solvent removed in vacuo. The crude product was purified by flash chromatography (silica gel; petroleum ether/dichloromethane 1:4) and further purified by twice recrystallising it from hexane to give a white solid.
Yield=0.10 g, (48%).
Compound 45:
2,3-difluoro-4-octyloxybiphenyl-$^{4'}$-yl
2-fluoro-4-((S)-2-fluorooctyloxy)benzoate A solution of compound 43 (0.25 g, 0.53 mmol). (S)-2-fluoro-octanol (0.078 g, 0.53 mmol) and diethylazodicarboxylate (0.111 g, 0.64 mmol) was prepared in 12 ml dry THF under nitrogen. To this was added slowly a solution of triphenylphosphine (0.167 g, 0.64 mmol) in 3 ml dry THF. The solution was stirred overnight at room temperature. The product was purified by flash chromatography (silica gel; petroleum ether/dichloromethane 1:2) and finally recrystallised from pentane at −20° C. to give a white solid.
Yield=0.26 g, (82%).
Compound 46:
2,3-difluoro-4-octyloxybiphenyl-4'-yl
2-fluoro-4-((S)-2-fluorooctanoyloxy)

This was prepared using a similar method to that described for compound 44. Quantities: compound 41 (0.201 g. 0.43 mmol), (S)-2-fluorooctanoic acid (0.069 g, 0.43 mmol), N,N-dimethylaminopyridine (0.013 g), dicyclohexylcarbodiimide (0.105 g, 0.51 mmol).
Yield=0.150 g. (57%).
Compound 47:
2,3-difluoro-4-octyloxybiphenyl-4'-yl
2-fluoro-4-((S)-2-fluorooctyloxy)benzoate.

This was prepared using a similar method to that described for compound 45. Quantities: compound 41 (0.220 g, 0.47 mmol), (S)-2-fluorooctanol (0.069 g, 0.47 mmol), diethylazodicarboxylate (0.097 g, 0.56 mmol), triphenylphosphine (0.147 g, 0.56 mmol).
Yield=0.20 g, (71%)
Compound 51:
3-fluoro-4-methoxycarbonyloxybenzoic acid.

This was prepared using the method according to the published procedure in Helv. Chim. Acta 67, 1987, 1578.
Compound 52:
2,3-difluoro-4-octoxybiphenyl-4'-yl
3-fluoro-4-methoxycarbonyloxybenzoate.

This was prepared using a similar method to that described for compound 12. Quantities: Compound 12 (0.781 g, 2.33 mmol), compound 51 (0.50 g, 2.33 mmol), diethylazodicarboxylate (0.488 g, 2.80 mmol), triphenylphosphine (0.733 g, 2.80 mmol).
Yield=0.526 g (43%)
Phase Transitions (°C.) K 84.0/103.8N 177.5 I Compound 53:
2,3-difluoro-4-octoxybiphenyl-4'-yl
3-fluoro-4-hydroxybenzoate.

This was prepared using a similar method to that described for compound 41. Quantities: Compound 52 (0.50 g, 0.94 mmol).
Compound 48:
2,3-difluoro-4-octoxybiphenyl-4'-yl
3-fluoro-4-(2-fluorooctyloxy)benzoate.

This was prepared using a similar method to that described for compound 45. Quantities: Compound 53 (0.180 g, 0.38 mmol), (S)-2-fluorooctanol (0.056 g, 0.38 mmol), diethylazodicarboxylate (0.080 g, 0.456 mmol), triphenylphosphine (0.120 g, 0.456 mmol)
Yield=0.163 g, (71%).
Compound 49:
2,3-difluoro-4-octoxybiphenyl-4'-yl
3-fluoro-$^4$-((S)-2-fluorooctanoyloxy)benzoate.

This was prepared using a similar method to that described for compound 44. Quantities: Compound 53 (0.199 g, 0.42 mmol), (S)-2-fluorooctanoic acid (0.068 g, 0.42 mmol, N,N-dimethylaminopyridine (0.013 g), dicyclohexylcarbodiimide (0.104 g, 0.50 mmol).
Yield=0.165 g, (64%).
Compound 54:
2',3-difluoro-4-octoxybiphenyl-4'-yl
3-fluoro-4-methoxycarbonyloxybenzoate.

This was prepared using a similar method to that described for compound 45. Quantities: Compound 38 (0.715 g, 2.14 mmol), compound 51 (0.458 g, 2.14 mmol), diethylazodicarboxylate (0.447 g, 2.57 mmol), triphenylphosphine (0.674 g, 2.57 mmol).
Yield=0.456 g, (40%).
Compound 55:
2',3-difluoro-4-octoxybiphenyl-4'-yl
3-fluoro-4-hydroxybenzoate.

This was prepared using a similar method to that described for compound 41. Quantities: Compound 54 (0.410 g, 0.77 mmol).
Yield=0.308 g, (84%),
mp=134°–36° C.
Compound 50:
2',3-difluoro-4-octoxybiphenyl-4'-yl
3-fluoro-4-((S)-2-fluorooctyloxy)benzoate.

This was prepared using a similar method to that described for compound 45. Quantities: Compound 55 (0.180 g. 0.38 mmol), (S)-2-fluorooctanol (0.056 g, 0.38 mmol), diethylazodicarboxylate (0.080 g, 0.46 mmol), triphenylphosphine (0.121 g, 0.46 mmol).
Yield =0.189 g, (83%).

TABLE 1

Phase transition temperatures

| Compound | °K. | $S_C^\circ$ | $S_A$ | $TGB_A^\circ$ | Ch | BPI | BPII | I |
|---|---|---|---|---|---|---|---|---|
| 22 | . | 98(l) | . | . | 133.4 | 153.3 | 154.2 | 155.5 |
| 23 | . | 93(l) | . | . | 141.7 | 162.0 | 162.7 | 163.3 |
| 24 | . | 124(l) | 157.4 | . | . | . | . | 171.1 |
| 25 | . | 104(r) | 156.6 | . | 173.7 | . | . | 175.7 |
| 30 | . | 105(l) | . | . | 141.9 | 155.5 | 155.6 | 155.6 |
| 31 | . | 77(r) | 134.5 | 144.4 | 145.3 | 159.5 | . | 160.2 |
| 33 | . | 86(l) | . | . | 120.9 | 136.6 | 137.4 | 137.5 |
| 44 | . | 93(l) | . | . | 121.1(r) | 146.8 | . | 146.9 |
| 45 | . | 84(r) | . | . | 113.8(r) | 145.5 | . | 147.2 |
| 46$^{(*1)}$ | . | 73(r) | 97.2 | . | 133.9(r) | . | . | 137.7 |

TABLE 1-continued

Phase transition temperatures

| Com- pound | °K. | $S_C°$ | $S_A$ | $TGB_A°$ | Ch | BPI | BPII | I |
|---|---|---|---|---|---|---|---|---|
| 47 | . | . | 38.0 | . | 140.5(r) | . | . | 144.2 |
| 48 | . | 102(r) | . | . | 146.0 | 152.9 | 152.9 | 153.8 |
| 49(¶¶) | . | 80.5(l) | . | . | 136.6 | . | . | 147.0 |
| 50 | . | 103.5(r) | 106.5 | . | . | . | . | 152.2 |

K = Crystalline, S = smectic. Ch = cholesteric, BP = blue phase, I = isotropic, r = right-handed twist, l = left-handed twist, $TGB_A$ = Twisted Grain Boundary A Phase.
Wherever possible, the source of the helicity in the chiral phases has been determined and this is shown in parantheses after the phase assignment, i.e. $S_C*(l)$ represents a chiral smectic C phase with a left-handed helix.
(¶)For compound 46 there is a helix inversion: $S_C*(r)$ 68.7° C. $S_C*(l)$.
(¶¶)For compound 49 there is an $N_\infty*$ phase:
$S_C*(l)$ 136.5 $N_\infty*$ 137.0 Ch(r) 147.0 I.
$N_\infty*$ is an infinite pitch cholesteric phase (i.e. unwound) and therefore necessarily nematic. For further details of this and related phenomena see J. Mater. Chem., 1992, 2(8), 805–810; and J. Mater. Chem., 1993, 3(4), 399–405.
$N_\infty*$ is where the pitch of the cholesteric phase is infinite but the mesophase still has chiral symmetry.

Figure 14:
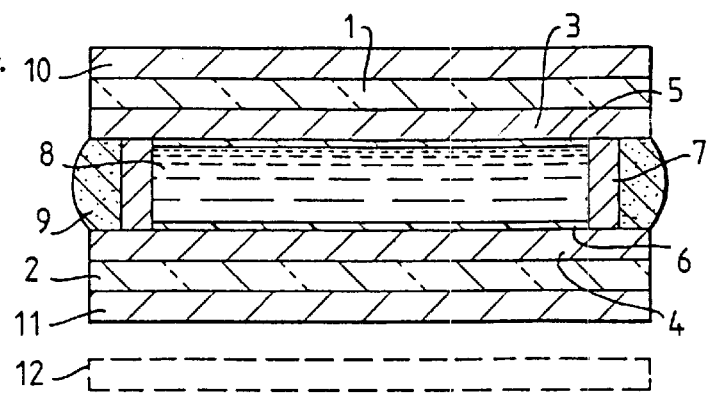
FIG. 14 illustrates a liquid crystal device.
Figure 15:
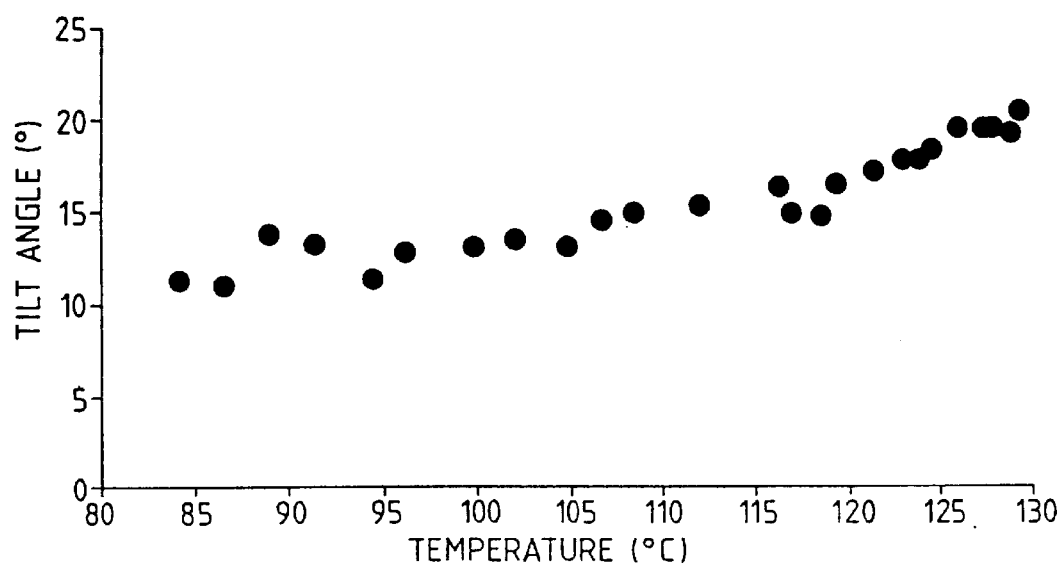
FIG. 15 is a graph of tilt angle (°) versus temperature (°C.) for compound 49.
Figure 16:
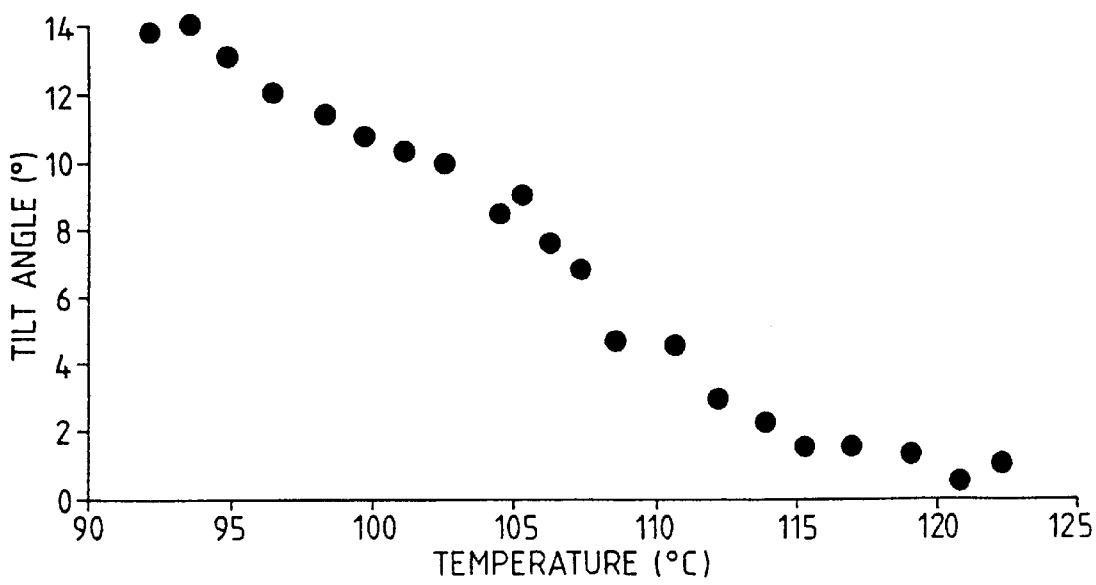
FIG. 16 is a graph of tilt angle (°) versus temperature (°C.) for compound 50.
Figure 17:
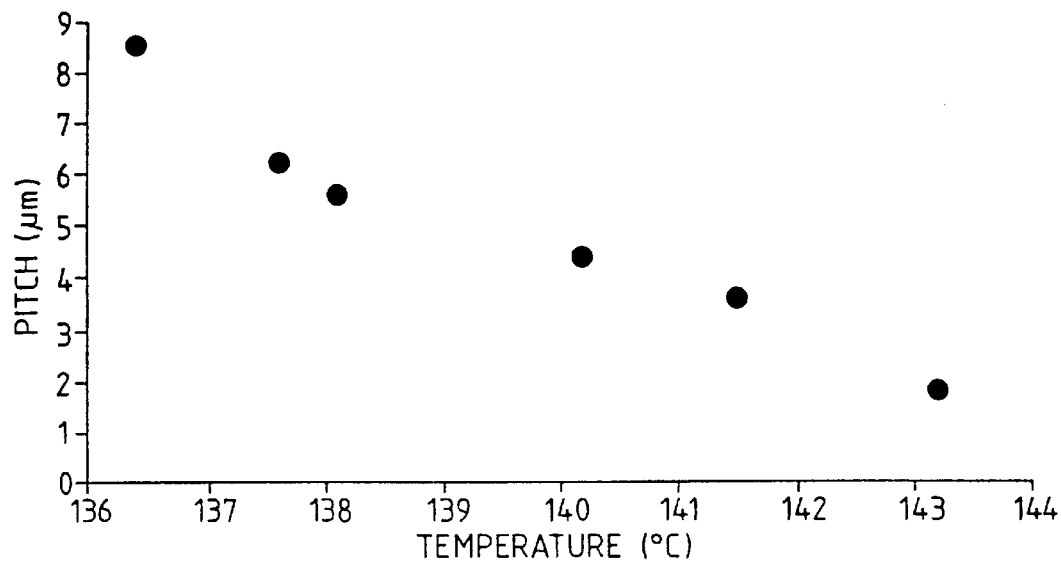
FIG. 17 is a graph of temperature (°C.) versus pitch ($\mu$m) in the cholesteric phase close to the infinite point for compound 49.
Figure 18:
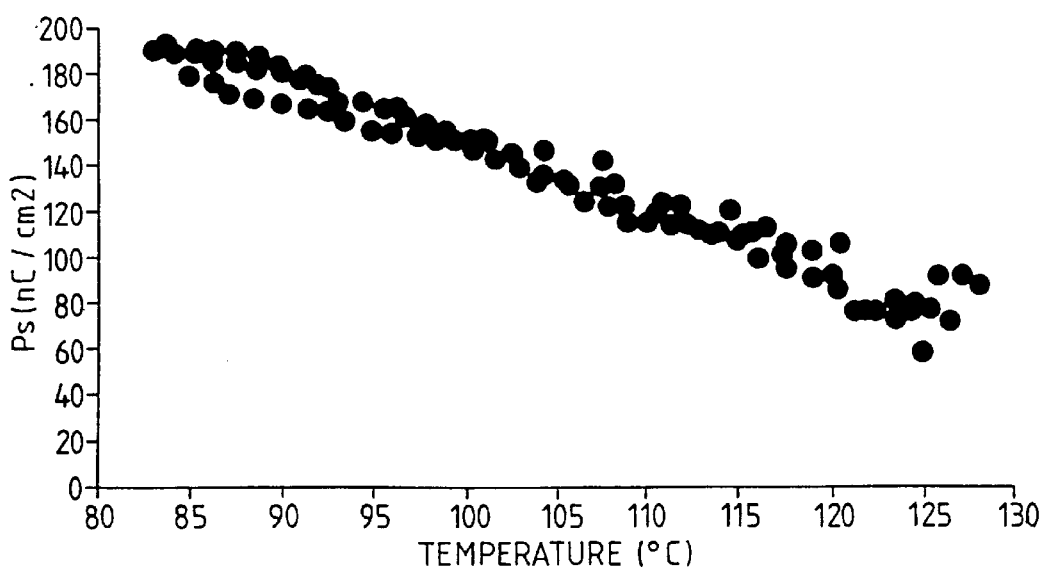
FIG. 18 is a graph of spontaneous polarisation (nC/cm$^2$) versus temperature (°C.) for compound 49. The plotted points are for three separate runs.

An example of the use of a compound of Formula I in a liquid crystal material and device embodying the present invention will now be described with reference to FIG. 14.

The liquid crystal device consists of two transparent plates, 1 and 2, in this case made from glass. These plates are coated on their internal face with transparent conducting electrodes 3 and 4. An alignment layer is introduced onto the internal faces of the cell so that a planar orientation of the molecules making up the liquid-crystalline material will be approximately parallel to the glass plates 1 and 2. This is done by coating the glass plates 1,2 complete with conducting electrodes 3,4 with layers of film 5 and 6 of a suitable polymer, eg polyimide. The electrodes 3,4 may be formed into row and column electrodes so that the intersections between each column and row form an x, y matrix of addressable elements or pixels. Prior to the construction of the cell the films 5,6 are rubbed with a soft tissue in a given direction, the rubbing directions being arranged parallel upon construction of the cell. A spacer 7 eg of polymethyl methacrylate separates the glass plates 1 and 2 to a suitable distance eg 2 microns. Liquid crystal material 8 is introduced between glass plates 1, 2 by filling the space in between them. The spacer 7 is sealed with an adhesive 9 in a vacuum using an existing technique. Polarisers 10, 11 are arranged in front of and behind the cell.

The device may operate in a transmissive or reflective mode. In the former, light passing through the device, eg from a tungsten bulb, is selectively transmitted or blocked to form the desired display. In the reflective mode a mirror (12) is placed behind the second polariser 11 to reflect ambient light back through the cell and two polarisers. By making the mirror partly reflecting the device may be operated both in a transmissive and reflective mode.

Tables 2–4, 6, 8–13 give values for the spontaneous polarisation (Ps) and Tables 5,7 and 14 for the tilt angle (°) over a range of temperatures for a number of the materials described by general formula I. The compounds of formula I are in some cases added to host materials. The following host material is given the abbreviation H1 and is a 1:1:1 mixture of the following:

$R_1=C_8, R_2=C_5$
$R_1=OC_8, R_2=C_5$
$R_1=OC_7, R_2=C_7$

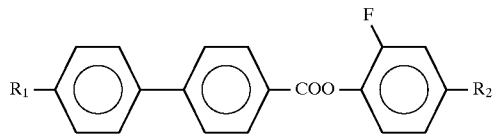

The host H1 is a commercially available smectic host, and is widely used in ferroelectric liquid crystal mixtures.

To measure the tilt angle a parallel 2 μm buffed polyimide (PI) coated cell was used. After aligning the material to achieve a uniform alignment by cooling from the isotropic phase through to the Sc phase a square wave of typically 5 V/μm at 50 Hz was applied.

Ps was measured in a 6 μm PI parallel cells, using a diamant bridge.

TABLE 2

| Temp/°C. | Ps/nC/cm² |
|---|---|
| 90 | 1.3 |
| 85 | 1.4 |
| 80 | 1.7 |
| 75 | 1.9 |
| 70 | 2.0 |
| 65 | 2.5 |
| 60 | 2.8 |
| 55 | 2.9 |
| 50 | 3.0 |
| 45 | 3.3 |
| 40 | 3.4 |

The data in Table 2 is for 4.6% of compound 22 in H1. Phase Transitions (°C.) K 98 $S_c*(l)$ 133.4 Ch 153.3 BPI 154.2 BPII 155.2 I

TABLE 3

| Temp/°C. | ps/nC/cm² |
|---|---|
| 100 | 1.5 |
| 95 | 3.0 |
| 90 | 4.0 |
| 85 | 5.0 |
| 80 | 5.5 |
| 75 | 6.0 |
| 70 | 7.0 |
| 65 | 7.4 |
| 60 | 8.2 |
| 55 | 8.6 |
| 50 | 9.1 |
| 45 | 9.6 |
| 40 | 10.2 |
| 35 | 10.6 |

The data in Table 3 is for 10% of compound 22 in H1. Phase Transitions (°C.): $S_c$ 101.9 Ch 151.1 I

TABLE 4

| Temp/°C. | Ps/nC/cm² |
|---|---|
| 95 | 6.0 |
| 90 | 6.9 |
| 85 | 9.5 |
| 80 | 10.5 |
| 75 | 11.0 |
| 70 | 11.5 |
| 65 | 12.7 |
| 60 | 13.8 |
| 55 | 14.0 |

TABLE 4-continued

| Temp/°C. | Ps/nC/cm$^2$ |
|---|---|
| 50 | 16.7 |
| 45 | 17.4 |
| 40 | 18.1 |

The data in Table 4 is for 15% compound 22 in H1.
Phase Transitions (°C.): S$_C$ 99.4 CH 149.3 I

TABLE 5

| Temp/°C. | tilt angle/° |
|---|---|
| 100 | 17 |
| 95 | 21 |
| 90 | 20 |
| 85 | 19 |
| 80 | 19.5 |
| 75 | 18.5 |
| 70 | 17.5 |
| 60 | 17.5 |
| 50 | 17.0 |
| 40 | 17.5 |

The data in Table 5 is for 5% compound 22 in H1.

TABLE 6

| Temp/°C. | Ps/nC/cm$^2$ |
|---|---|
| 130 | 49.3 |
| 125 | 55.6 |
| 120 | 61.8 |
| 115 | 65.7 |
| 110 | 70.8 |
| 105 | 74.7 |
| 100 | 85.3 |
| 95 | 89.4 |
| 107 | 80.0 |

The data in Tables 6 and 7 is for compound 23.
Phase Transitions (°C.): K 93 S$_C$*(r) 141.7 Ch 162.0 BPI 162.7 BPII 163.3 I.

TABLE 7

| Temp/°C. | tilt angle/° |
|---|---|
| 130 | 24 |
| 125 | 25.5 |
| 120 | 18 |
| 115 | 17 |
| 110 | 18 |
| 105 | 17 |
| 100 | 18 |
| 95 | 18 |

TABLE 8

| Temp/°C. | Ps/nC/cm$^2$ |
|---|---|
| 95 | 1.8 |
| 90 | 1.9 |
| 85 | 2.0 |
| 80 | 2.1 |
| 75 | 2.1 |
| 70 | 2.1 |
| 65 | 2.0 |
| 60 | 1.66 |
| 55 | 1.65 |
| 50 | 1.43 |

TABLE 8-continued

| Temp/°C. | Ps/nC/cm$^2$ |
|---|---|
| 45 | 1.32 |
| 40 | 1.28 |

The data in Table 8 if for 10% of compound 23 in H1.
Phase Transitions (°C.): S$_C$ 153.0 I

TABLE 9

| Temp/°C. | Ps/nC/cm$^2$ |
|---|---|
| 150 | 44.2 |
| 145 | 68.3 |
| 140 | 84.5 |
| 135 | 95.9 |
| 130 | 107.0 |
| 125 | 117.3 |
| 127 | 113.1 |

The data in Table 9 is for compound 24
Phase Transitions (°C.): K 124 S$_C$*(1) 157.4 S$_A$ 171.1 I

TABLE 10

| Temp/°C. | Ps/nC/cm$^2$ |
|---|---|
| 150 | 17.1 |
| 148 | 21 |
| 146 | 24.2 |
| 144 | 28.8 |
| 135 | 35.4 |
| 130 | 38.8 |
| 125 | 42.0 |
| 120 | 44.6 |
| 115 | 47.2 |
| 110 | 49.5 |
| 105 | 51.5 |

The data in Table 10 is for compound 25
Phase Transitions (°C.): K 104 S$_C$*(r) 156.6 SA 173.6 TGB A* 173.8 Ch 175.7 I

TABLE 11

| Temp/°C. | Ps/nC/cm$^2$ |
|---|---|
| 135 | 85 |
| 132 | 85 |
| 130 | 95 |
| 125 | 105 |
| 120 | 115 |
| 115 | 125 |
| 110 | 135 |
| 105 | 143 |

The data in Table 11 is for compound 30
Phase Transitions (°C.): K 105 S$_C$*(1) 141.9 Ch 155.5 BPI 155.6 BPII 155.6 I

TABLE 12

| Temp/°C. | ps/nC/cm$^2$ |
|---|---|
| 136 | 7.5 |
| 130 | 24 |
| 126 | 30 |
| 120 | 37 |
| 116 | 41 |
| 110 | 45.5 |
| 106 | 48 |

TABLE 12-continued

| Temp/°C. | ps/nC/cm² |
|---|---|
| 100 | — |
| 96 | 56 |
| 90 | 60 |
| 86 | 63.5 |
| 80 | 65.5 |
| 76 | 66.5 |
| 70 | 69 |
| 66 | 70 |

The data in Table 12 is for compound 31

Phase Transitions (°C.): K 77 $S_C^*$ 134.5 $S_A$ 144.4 TGB A* 145.3 Ch 159.5 BPI

TABLE 13

| Temp/°C. | Ps/nC/cm² |
|---|---|
| 116 | 1.2 |
| 110 | 4.0 |
| 106 | 5.0 |
| 100 | 5.5 |
| 96 | 5.8 |
| 90 | 6.4 |
| 86 | 6.6 |
| 80 | 6.6 |
| 76 | 6.7 |

The data in Table 13 is for compound 33

Phase Transitions (°C.): K 86 $S_C^*$(1) 120.9 Ch 136.6 BPI 137.4 BPII 137.5 I

TABLE 14

| Temp/°C. | tilt angle/° |
|---|---|
| 140 | 18.5 |
| 135 | 26.5 |
| 130 | 29.5 |
| 125 | 30.0 |
| 120 | 30.5 |
| 110 | 32.0 |

The data in Table 14 is for compound 48.

We claim:

1. A compound having a formula I

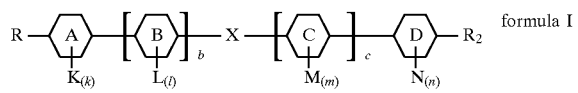

in which R is selected from alkyl, alkoxy or alkenyl and contains 1–20 carbon atoms;

A, B, C, D are independently selected from phenyl, cyclohexyl, pyridyl, pyrimidyl; b is independently selected from 0, 1 or 2; c is independently selected from 0 or 1 provided that the total of b+c is not greater than 2;

K, L, M, N are independently selected from the halogen group;

(k), (1), (m), (n) are independently selected from 0, 1, 2, 3 or 4;

provided that at least one of the groups A, B, C, D present is a phenyl group with at least one fluorine substituted on it;

X is selected from OCO, COO, OCH₂, CH₂O, CH₂CH₂;

$R_2$ is selected from the following:

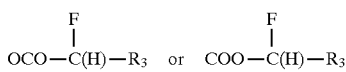

$R_3$ is a linear alkyl group containing 1–15 carbon atoms;
$R_2$ may also be the following:

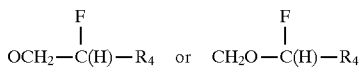

$R_4$ is a linear or branched chain alkyl group containing 1–15 carbon atoms provided that when $R_2$ is selected from $$OCH_2-C(H)-R_4 \quad \text{or} \quad CH_2O-C(H)-R_4$$
(with F substituent)

then b+c=1 or 2 and A, B, C, D groups are phenyl groups.

2. A compound according to claim 1 wherein whichever of A, B. C, D are present are selected from phenyl.

3. A compound according to claim 2 wherein X is COO or OCO.

4. A compound according to claim 3 wherein whichever of K. L, M, N present are selected from fluorine.

5. A liquid crystal device comprising a layer of liquid crystal material contained between two spaced cell walls each bearing electrode structures and surface treated on facing surfaces to align liquid crystal material molecules, characterised in that the liquid crystal material includes the compound as described in claim 1.

6. A liquid crystal mixture containing any of the compounds of claim 1 and a host material of the following general formula:

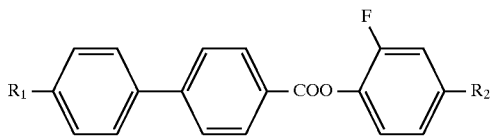

where $R_1$ and $R_2$ are independently $C_3$–$C_{12}$ alkyl or alkoxy.

7. A liquid crystal mixture containing any of the compounds of claim 1 and a host material of the following general formula:

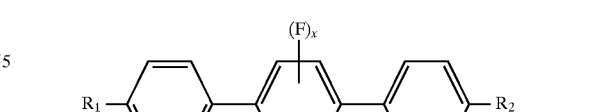

where $R_1$ and $R_2$ are independently $C_3$–$C_{12}$ alkyl or alkoxy x is 1 and F may be on any one of the available substitution positions on the phenyl ring specified.

8. A liquid crystal mixture containing any of the compounds of claim 1 and a host material of the following general formula:

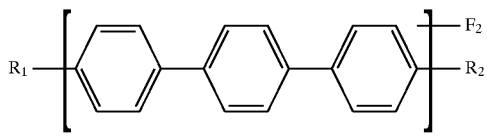

where $R_1$ and $R_2$ are independently $C_{3-12}$ alkyl or alkoxy.

9. A liquid crystal mixture containing any of the compounds of claim 1 and a host material of the following genera formula:

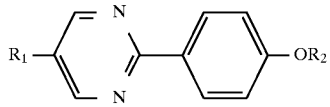

where $R_1$ is $C_{3-12}$ alkyl and $R_2$ is given by the general formula $(CH_2)_n\text{–}CHXCH_2CH_3$, where n is 1 to 5 and X is CN or Cl.

10. A liquid crystal mixture containing any of the compounds of claim 1 and a host material of the following general formula

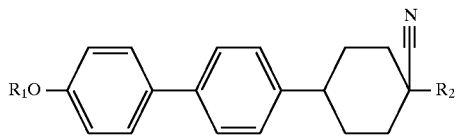

where $R_1$ and $R_2$ are independently $C_1$–$C_{15}$ alkyl.

11. A liquid crystal mixture containing any of the compounds of claim 1 and a host material of the following general formula:

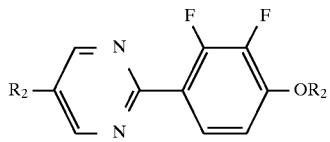

where $R_1$ and $R_2$ are independently $C_3$–$C_9$ alkyl.

12. A device according to claim 5 including a host material of the following formula:

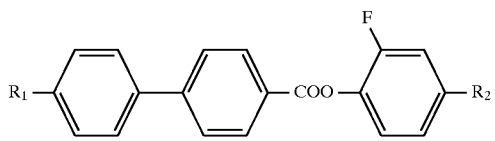

where $R_1$ and $R_2$ are independently $C_3$–$C_{12}$ alkyl or alkoxy.

13. A device according to claim 5 including a host material of the following formula:

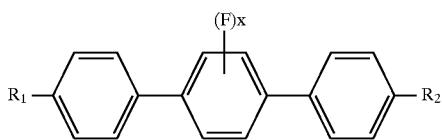

where R and $R_2$ are independently $C_3$–$C_{12}$ alkyl or alkoxy, x is 1 and F may be on any one of the available substitution positions on the phenyl ring specified.

14. A device according to claim 5 including a host material of the following formula:

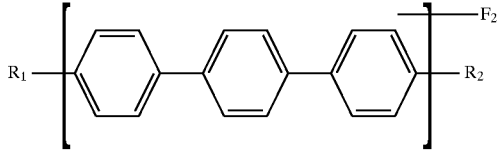

where $R_1$ and $R_2$ are independently $C3$–$C_{12}$ alkyl or alkoxy.

15. A device according to claim 5 including a host material of the following formula:

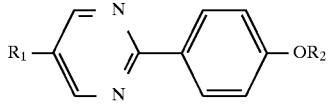

where $R_1$ is $C_3$–$C_{12}$ alkyl and $R_3$ is given by the formula $(CH_2)_n\text{—}CHXCH_2CH_3$, where n is 1 to 5 and X is CN or Cl.

16. A device according to claim 5 including a host material of the following formula:

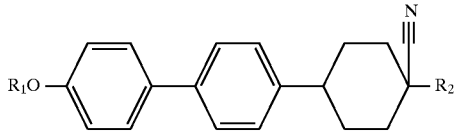

where $R_1$ and $R_2$ are independently $C_1$–$C_2$ alkyl.

17. A device according to claim 5 including a host material of the following formula:

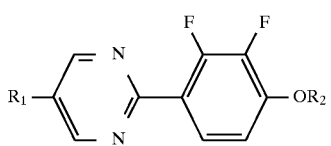

where $R_1$ and $R_2$ are independently $C_3$–$C_9$ alkyl.

* * * * *